(12) United States Patent
Jurisson et al.

(10) Patent No.: US 9,427,483 B2
(45) Date of Patent: Aug. 30, 2016

(54) RADIOISOTOPE TRITHIOL COMPLEXES

(71) Applicants: Silvia S. Jurisson, Columbia, MO (US); Cathy S. Cutler, Columbia, MO (US); Anthony J. Degraffenreid, Columbia, MO (US)

(72) Inventors: Silvia S. Jurisson, Columbia, MO (US); Cathy S. Cutler, Columbia, MO (US); Anthony J. Degraffenreid, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 14/679,520

(22) Filed: Apr. 6, 2015

(65) Prior Publication Data
US 2015/0283274 A1    Oct. 8, 2015

Related U.S. Application Data

(60) Provisional application No. 61/995,193, filed on Apr. 4, 2014, provisional application No. 62/070,998, filed on Sep. 10, 2014.

(51) Int. Cl.
*A61K 51/04* (2006.01)
*A61K 51/10* (2006.01)

(52) U.S. Cl.
CPC ....... *A61K 51/0478* (2013.01); *A61K 51/1093* (2013.01)

(58) Field of Classification Search
CPC ................ A61K 51/0478; A61K 51/1093; A61K 51/1096
See application file for complete search history.

(56) References Cited

FOREIGN PATENT DOCUMENTS

| CN | 104151397 A | 11/2014 |
|---|---|---|
| WO | WO 92/11253 | 7/1992 |

OTHER PUBLICATIONS

Vandenbroucke, A.C., Jr. et al., "Polycyclic Group V Ligands. IV. 2,6,7-Trithia-4-methyl-1-phosphabicyclo-[2.2.2]octane and Derivatives", *Inorganic Chemistry*, Jul. 1968, pp. 1469-1472, vol. 7, No. 7 (4 pgs).
Camerano, Jose' A., et al., "A Trithiol Protio-Ligand and Its Fixation to the Periphery of a Carbosilane Dendrimer as Scaffolds for Polynuclear Rhodium and Iridium Complexes and Metallodendrimers", *Organometallics*, 2005, pp. 1547-1556, vol. 24, No. 21, Copyright 2005 American Chemical Society, Published on Web Sep. 8, 2005 (10 pgs).
Garg, Niti et al., "Robust Gold Nanoparticles Stabilized by Trithiol for Application in Chemiresistive Sensors", *Nanotechnology* 21 (2010), IOP Publishing, Published Sep. 8, 2010, Copyright 2010 IOP Publishing Ltd. (7 pgs).
Li, N., "Synthesis and characterization of rhodium 105 labeled thiamacrocycles for use to formulate peptide receptor agents", (1996) (Available from Dissertations & Theses @ University of Missouri—Columbia. (304275518), Copyright 1999, UMI Company (159 pgs).
Maki, Y. et al., "The Separation of Arsenic-77 in a Carrier-Free State from the Parent Nuclide Germanium-77 by a Thin-Layer Chromatographic Method", *Journal of Radioanalytical Chemistry*, 1974, pp. 5-12, vol. 22, Issue 1-2 (10 pgs).
Wojczykowski, Klaus et al., Amphiphilic Trithiols RC (CH$_2$SH)$_3$, SYNLETT 2006, No. 1, pp. 39-40, Online Publication, Dec. 16, 2005, Copyright Thieme Stuttgart (2 pgs).
Jennewein, M., et al., "A new method for radiochemical separation of arsenic from irradiated germanium oxide", *Applied Radiation and Isotopes* 63, (2005) pp. 343-351 (2005), Copyright 2005 Published by Elsevier Ltd. (9 pgs).
Bokhari, T., et al., "Separation of no-carrier-added arsenic-77 from neutron irradiated germanium", *Radiochim. Acta*, 97, pp. 503-506 (2009), Copyright Oldenbourg Wissenschaftsverlag (4 pgs).

*Primary Examiner* — Audrea Buckley
(74) *Attorney, Agent, or Firm* — Stinson Leonard Street LLP

(57) ABSTRACT

The present invention is directed to a series of stable radioisotope trithiol complexes that provide a simplified route for the direct complexation of radioisotopes present in low concentrations. In certain embodiments, the complex contains a linking domain configured to conjugate the radioisotope trithiol complex to a targeting vector. The invention is also directed to a novel method of linking the radioisotope to a trithiol compound to form the radioisotope trithiol complex. The inventive radioisotope trithiol complexes may be utilized for a variety of applications, including diagnostics and/or treatment in nuclear medicine.

20 Claims, 10 Drawing Sheets

RADIOISOTOPE TRITHIOL COMPLEXES

CROSS-REFERENCE TO RELATED APPLICATIONS

This application is based on and claims priority to U.S. Provisional Application Ser. No. 61/995,193, filed on Apr. 4, 2014, and U.S. Provisional Application Ser. No. 62/070,998, filed on Sep. 10, 2014, each of which is incorporated herein by reference in its entirety.

STATEMENT REGARDING FEDERALLY SPONSORED RESEARCH OR DEVELOPMENT

This invention was made with Government support under Grant No. DE-SC0003 85 1 awarded by the Department of Energy. The Government has certain rights in the invention.

BACKGROUND OF THE INVENTION

1. Field of the Invention

The present invention relates to the field of diagnostic imaging and radiotherapy technology, more specifically, to a series of radioisotope trithiol complexes.

2. Description of Related Art

An underlying theme of nuclear medicine is the radiotracer principle. This principle uses a radiolabeled molecule (radiopharmaceutical) in extremely low concentrations (often μM or less depending on half-life) for imaging and treatment of disease. The use of a trace amount of material avoids toxicological effects often observed at the macroscopic level, and often found in pharmaceuticals. Several FDA approved radiopharmaceuticals are currently in use using this underlying concept.

Utilization of the radioisotopes at trace levels often requires the development of a chelate with high in vivo stability that can be linked to a targeting vector such as a peptide or monoclonal antibody. However, the development of such complexes has been challenging. The radioisotopes are present in low concentrations, often at nanomolar concentrations, making it difficult to create a stable complex. Further all chemical derivatizations, conjugation to targeting vectors, transport and in vivo delivery must occur within the half-life of the radioisotope. Thus, radioisotopes used in such complexes preferably have relatively long half-lives to permit chemical derivatization and linkage to targeting vectors prior to in vivo use. These challenges are not present in macroscopic approaches to chelating the stable isotopes of the radioisotopes.

Radioisotopes of arsenic, $^{71, 72, 74, 77}$As' have relatively long half-lives compared to traditional radionuclides such as $^{18}$F, $^{99m}$Tc, $^{89}$Sr, $^{90}$Y, $^{111}$In and $^{153}$Sm. These radioarsenic isotopes have suitable half-lives to permit chemical derivatization and in vivo localization using monoclonal antibodies (mAbs) and proteins for imaging and therapy. Arsenic radioisotopes include the positron emitters, $^{71}$As ($t_{1/2}$ 64.8 h, 32%, Eβ+max 2.0 MeV), $^{72}$As ($t_{1/2}$ 26.4 h, 88%, Eβ+max 2.5 MeV), $^{74}$As ($t_{1/2}$ 17.8 d, 29%, Eβ+max 0.94 MeV), and a beta emitter, $^{77}$As ($t_{1/2}$ 38.4 h, 100% 13+, Eβ-max 0.68 MeV), giving them the ability to be used as 'matched pair' radioisotopes for positron emission tomography (PET) and radiotherapy. The positron emitters are available through the bombardment of various targets using an accelerator or cyclotron. The beta emitter, $^{77}$As, can be produced through the irradiation of an enriched $^{76}$Ge target to produce $^{77}$Ge ($t_{1/2}$ 11.6 h, 100% β−), which decays to no-carrier added $^{77}$As. While several production and separation methods for radioarsenic compounds have been developed, little work in stably complexing radioarsenic has been performed.

Utilization of these radioisotopes of arsenic requires the development of a chelate with high in vivo stability that can be linked to a targeting vector such as a peptide or mAb. A survey of current literature only revealed two attempts at stably complexing no-carrier added arsenic. The first was done by Jahn et al. using an N2S$_2$ monoamine-monoamide (MAMA) chelator, and they concluded that the radioarsenic was quantitatively complexed, which has not been further confirmed. The second was carried out in high yield by Jennewein et al. by directly labeling a sulfhydryl modified mAb using $^{74177}$AsI$_3$. It was determined that the sulfhydryl modification caused no inhibition of the immunoreactivity of the mAb and the labeled complex was stable for up to 72 h in fetal bovine serum. In a later publication by Jennewein et al. they utilized this labeled antibody to successfully image subcutaneous Dunning prostate tumors in rats. However, there is a need to develop a stable radioarsenic complex, which employs a stable chelate and provides a simplified route for the direct complex of radioarsenic and other radioisotopes.

BRIEF SUMMARY OF THE INVENTION

One aspect of the invention is directed to series of stable radioisotope trithiol complexes.

One aspect of the invention is directed to a stable radioisotope trithiol complex conjugated to a targeting vector.

Another aspect of the invention is directed to methods for making the stable radioisotope trithiol complexes and conjugating the complexes with the targeting vector.

Another aspect of the invention is directed to methods for using the stable radioisotope complex of the invention.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1A:
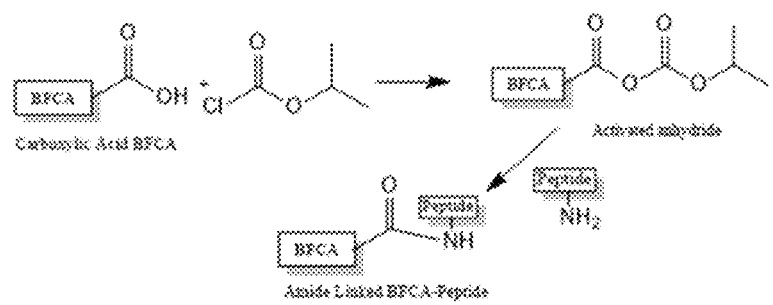
FIG. 1a depicts examples of reactions of activated functional groups with biomolecular side chains and FIG. 1b depicts certain exemplary functional groups consistent with the present invention.
Figure 1A:
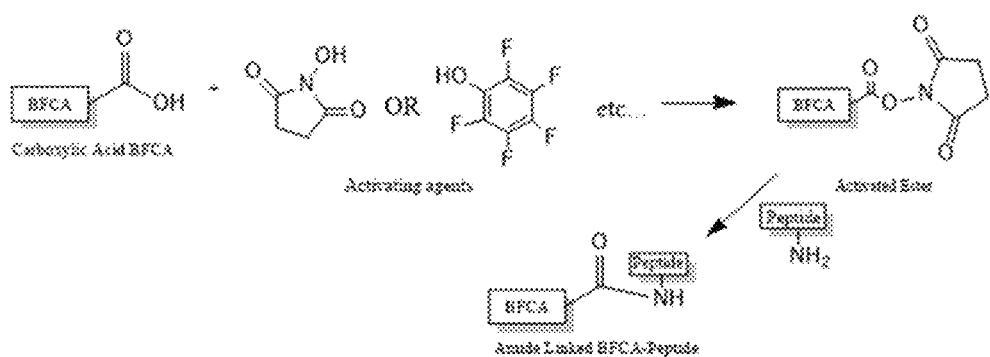
Figure 1A:
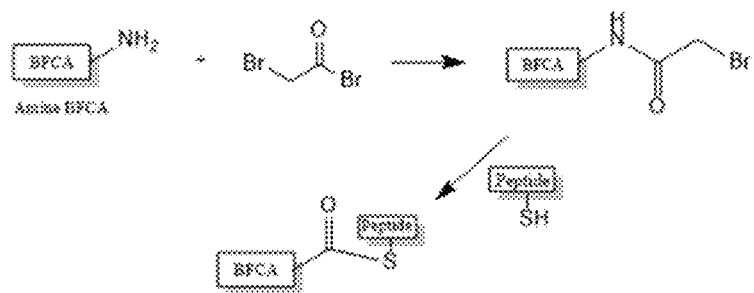
Figure 1A:
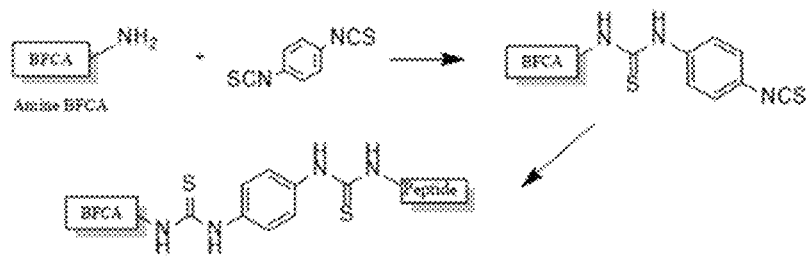

The present invention is directed to a series of stable radioisotope trithiol complexes that provide a simplified route for the direct complexation of radioisotopes present in low concentrations. In certain embodiments, the complex contains a linking domain configured to conjugate the radioisotope trithiol complex to a targeting vector. The invention is also directed to a novel method of linking the radioisotope to a trithiol compound to form the radioisotope trithiol complex. The inventive radioisotope trithiol complexes may be utilized for a variety of applications, including diagnostics and/or treatment in nuclear medicine.

One embodiment of the present invention is directed to a radioisotope trithiol complex of Formula (I):

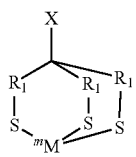

wherein each $R_1$ is independently a substituted or unsubstituted $C_1$ to $C_5$ hydrocarbyl;

$^mM$ is a radioisotope; and

X is a chemical moiety.

In certain embodiments of the invention, the radioisotope $^mM$ is selected from the group consisting of a radioisotope of arsenic, lead, mercury, silver, copper, platinum, lanthanides, actinides, rhenium, nickel, bismuth, technetium, gallium, rhodium and zinc. The radioisotope $^mM$ may be a no carrier added (NCA) isotope. In the exemplary embodiments described herein, each radioisotope $^mM$ is linked to all three sulfur atoms of a single trithiol compound, and each radioisotope $^mM$ is linked to only one trithiol compound. However, other exemplary $^mM$ radioisotopes, such as $^mRe$ or $^mTc$, may coordinate with two trithiol compounds.

In certain exemplary embodiments, the radioisotope $^mM$ is a radioisotope of arsenic. Radioisotopes of arsenic include $^{71}As$, $^{72}As$, $^{74}As$, and $^{77}As$. $^{77}As$ is generally used for radiotherapy. Available species of $^{77}As$ include $AsCl_3$, $AsBr_3$, $AsI_3$ and other trivalent arsenic species. $^{72}As$ is generally used for imaging. Various isotopes of arsenic are described in Jennewein, M., et al., *A new method for radiochemical separation of arsenic from irradiated germanium oxide*, Applied Radiation and Isotopes 63, 343-51 (2005), which is incorporated by reference for the disclosure of such isotopes, including the method of making them.

In certain exemplary embodiments, each $R_1$ group of the trithiol complex of the present invention is an alkyl and may be a single methyl group. In certain embodiments each $R_1$ has the same number of carbon atoms. However, each $R_1$ may have differing numbers of carbon atoms. Each $R_1$ may independently be substituted or unsubstituted alkyl, alkenyl or alkynyl. However, each $R_1$ may have no substitutions, may have the same or different substitutions, and/or may have the same or different degree of saturation.

The compound of Formula I is configured such that X can be any chemical moiety bound to the central carbon of the radioisotope trithiol complex. In certain embodiments, X is H or a substituted or unsubstituted, saturated or unsaturated hydrocarbyl that may contain heteroatoms within the hydrocarbyl chain.

In certain embodiments, X is a linking domain. Linking domain X of the present invention is any chemical structure configured to link the central carbon of the radioisotope trithiol complex to a targeting vector. In certain exemplary embodiments, linking domain X comprises a functional group to facilitate linkage to the targeting vector. Linking domain X may also be water soluble to increase the solubility of the radioisotope trithiol complex. In certain embodiments linking domain X may contain a spacer between the central carbon atom of the trithiol complex and the functional group.

Figure 1B:
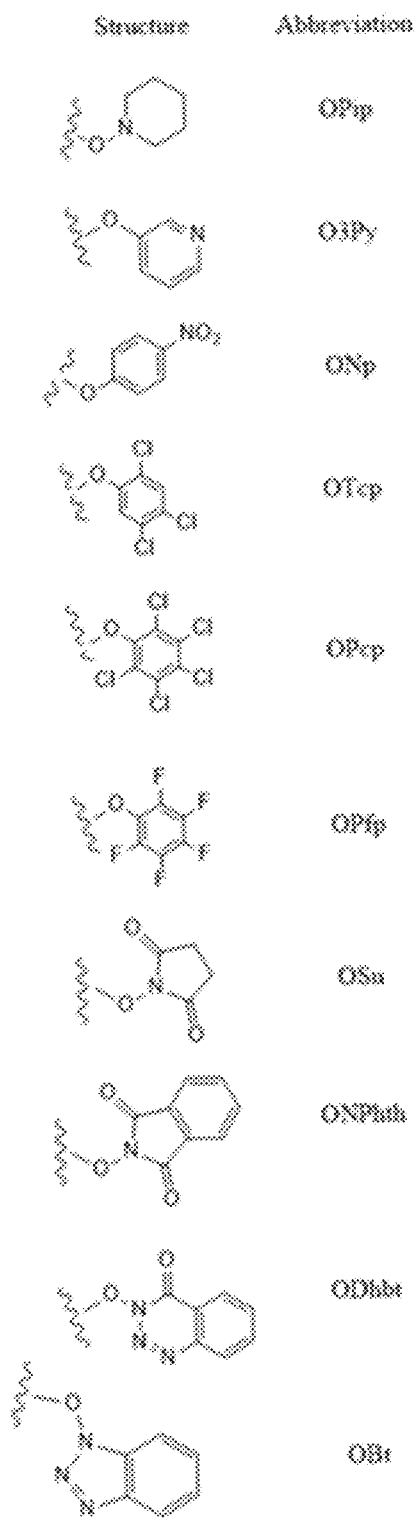
Figure 2:
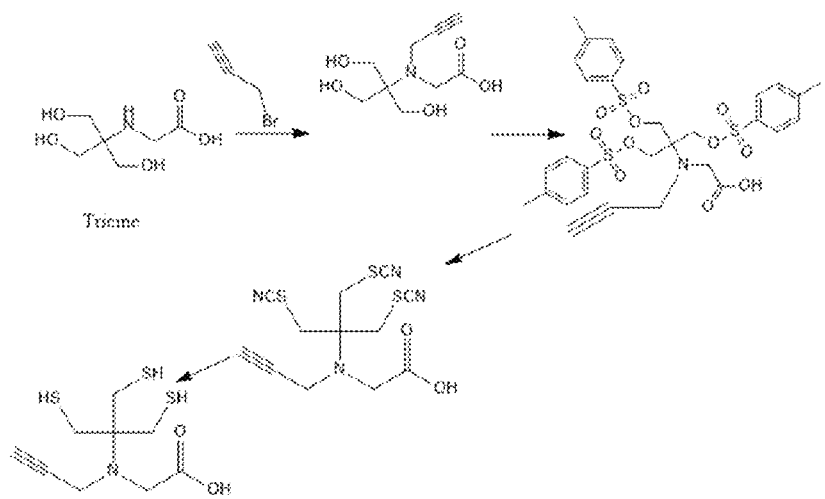
FIG. 2 depicts a proposed reaction scheme for synthesizing an exemplary compound of Formula V.
Figure 3:
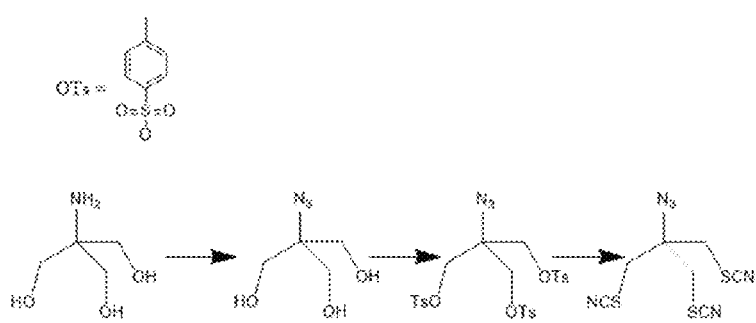
FIG. 3 depicts a proposed reaction scheme for synthesizing an exemplary protected compound of Formula V.
Figure 4:
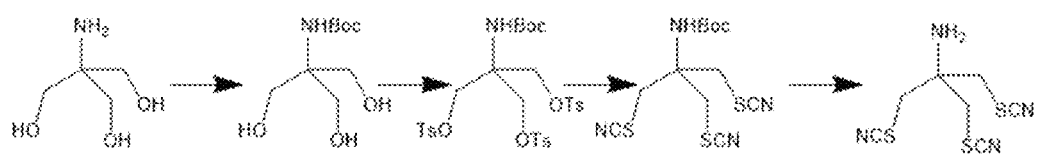
FIG. 4 depicts a proposed reaction scheme for synthesizing an exemplary protected compound of Formula V.
Figure 5:
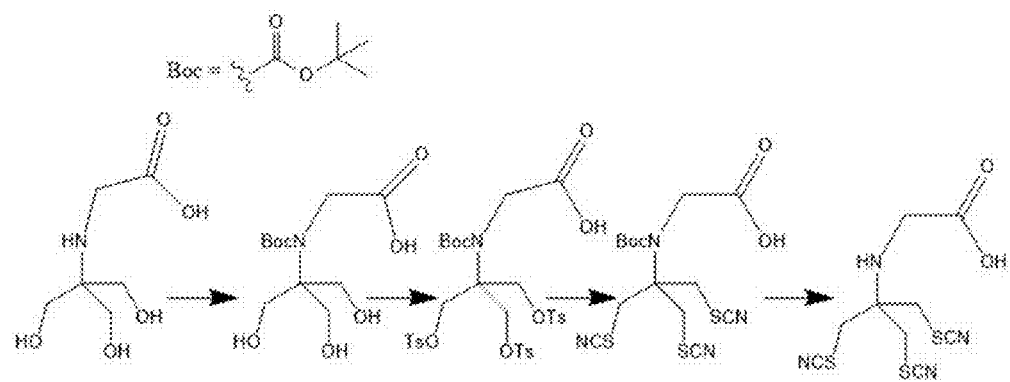
FIG. 5 depicts a proposed reaction scheme for synthesizing an exemplary protected compound of Formula V.
Figure 6:
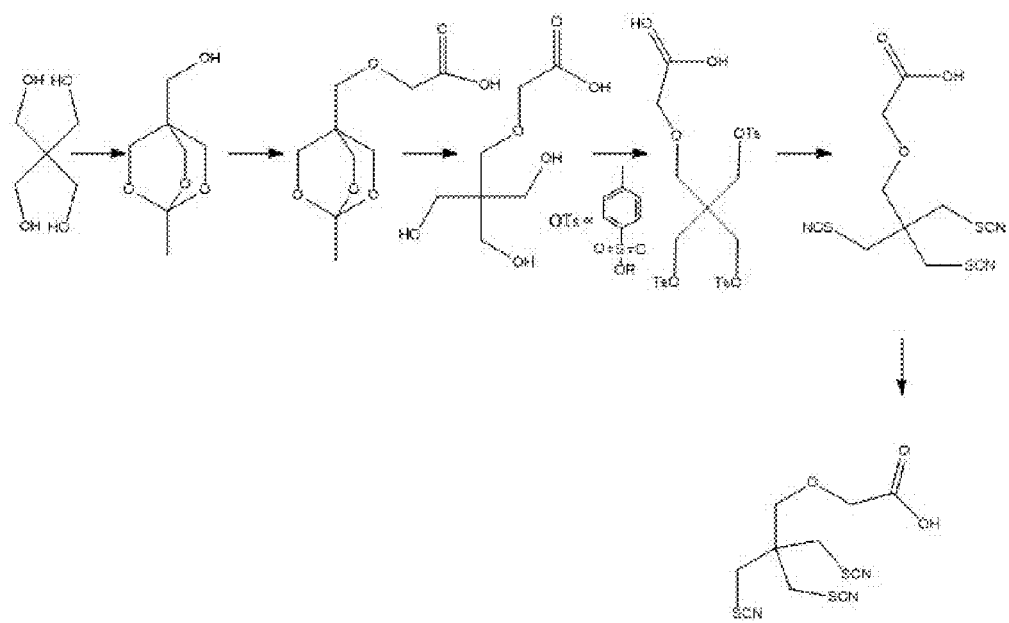
FIG. 6 depicts a proposed reaction scheme for synthesizing an exemplary protected compound of Formula V.
Figure 7:
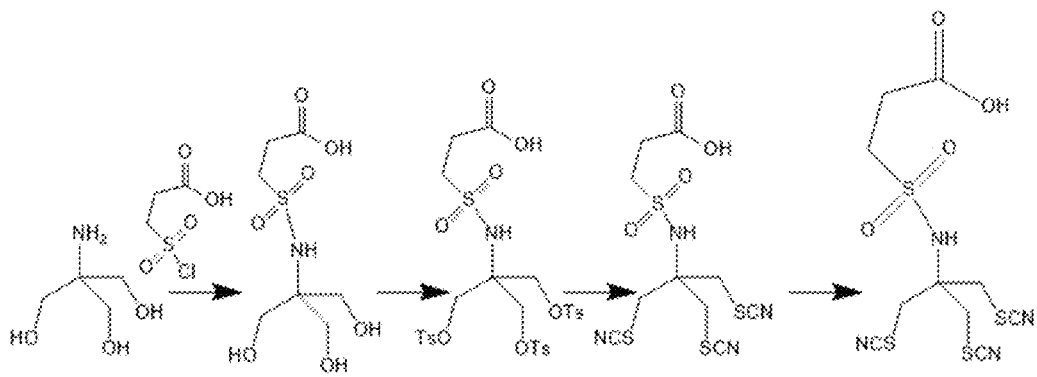
FIG. 7 depicts a proposed reaction scheme for synthesizing an exemplary protected compound of Formula V.

The functional group of linking domain X may be any functional group that will facilitate binding of the radioisotope trithiol complex to a targeting vector. The choice of a functional group will depend in part on the targeting vector to be used. Suitable functional groups will be readily understood by those of ordinary skill in the art. Suitable functional groups may include those shown in FIGS. 1a and 1b, which may be used with other vectors in addition to peptides. Other exemplary functional groups are described in various literature references, including Li, N., *Synthesis and characterization of rhodium $^{105}$ labeled thiamacrocycles for use to formulate peptide receptor agents* (1996) (Available from Dissertations & Theses @ University of Missouri—Columbia. (304275518)), Wong, S. and Jameson, D., Chemistry of Protein and Nucleic Acid Cross-Linking and Conjugation ($2^{nd}$ Ed.), CRC Press (2012), Wuts, P. and Greene, T., Greene's Protective Groups in Organic Synthesis ($4^{th}$ Ed.), John Wiley & Sons, Inc. (2007), Williams, P., et al., Chemical Approaches to the Synthesis of Peptides and Proteins, CRC Press (1997), Gross, E., and Meienhofer, J., The Peptides-Analysis, Synthesis, Biology ($1^{st}$ Ed.)(Vol. 1): Major Methods of Peptide Bond Formulation, Academic Press, Inc. (1979), Aime, S. et al., *Ch. 19 Chemistry of Molecular Imaging: An Overview*, Molecular Imaging: Principles and Practice (Weissleder, R., ed.), People's Medical Publishing House-USA (2010), Guillier, F., et al., *Linkers and Cleavage Strategies in Solid-Phase Organic Synthesis and Combinatorial Chemistry*, Chem. Rev., 100, 2091-2157 (2000), Albericio, A., et al., *Therapeutic Peptides*, Future Med. Chem. 4(12), 1527-1531 (2012) and Hamzeh-Mivehroud, M., et al., *Phage display as a technology delivering on the promise of peptide drug discovery*, Drug Discovery Today, 18(23/24), 1144-1157 (2013), which are incorporated by reference with respect to their disclosure of spacers, functional groups and their linkage to vectors. In certain exemplary embodiments, the functional group is selected from the group consisting of phosphonic acid, isothiocyanate, maleimide, carboxylic acid, primary amine, aldehyde, sulfonyl chloride, secondary amine, hydroxide, aryl-NCS, alkene, alkyne, azide, active esters, thiol, $CH_2OH$, $CH_2OCH_3$, $CH_2OCOCH_3$, $COOC_2H_5$, $CONHC_3H_7$, CO-Phe-$OC_2H_5$, CO-Phe-OH, CO-Phe-Ala-OH, CO-Phe-Met-$OCH_3$, and CO-Phe-Phe-Gly-Leu-Met-$NH_2$, where the Phe, Gly, Leu, Met, and Ala are amino acids. Certain exemplary active esters contain groups such as NHS, sulfo- NHS and other derivatives, and OSu. However any functional groups now known or hereafter developed that may be incorporated into linking domain X and are suitable for conjugation for the intended use can be used consistent with the present invention.

Linking domain X may contain a spacer, which may be any linkage connecting the central carbon of the trithiol to the functional group, as will be readily understood by one of ordinary skill in the art, or a spacer may not be present. In certain embodiments, the spacer may be a substituted or unsubstituted, saturated or unsaturated hydrocarbyl that may contain heteroatoms within the hydrocarbyl chain. Exemplary embodiments of the spacer include substituted or unsubstituted alkyl, substituted or unsubstituted aryl, amino acid, polyethylene glycol, isothiocyanate, a sulfate group, an amide group or a phosphate group. Certain other exemplary spacers are described in the references cited in the previous paragraph. However any spacers now known or hereafter developed that may be incorporated into linking domain X and are suitable for the intended use can be used consistent with the present invention.

In certain exemplary embodiments, linking domain X may be selected from the group consisting of $R_2$—Y, $R_2$—O—$R_2$—Y, $R_2$—N—$(R_2)_2$—Y, wherein each $R_2$ is independently a substituted or unsubstituted, saturated or unsaturated hydrocarbyl, and Y is a functional group, as described above. In embodiments wherein X contains an N heteroatom, one of the $R_2$ groups may be hydrogen.

The radioisotope trithiol complex of the present invention may be conjugated to a targeting vector. In certain exemplary embodiments, the targeting vector is conjugated to the functional group of linking domain X. Targeting vectors may be conjugated to the radioisotope trithiol complex via covalent bonds. The nature of the targeting group will depend on the intended use of the radioisotope trithiol complex, as will be readily understood by one of ordinary skill in the art. Certain exemplary targeting vectors include peptides, antibodies, oligonucleotides, carbohydrates, lipids, and organic molecules.

In certain embodiments, the targeting vector is a peptide or antibody. Suitable peptides include targeting peptides, such as bombesin (BBN), BBN (7-14), RM2 (as described in Mansi, R. et al., *Development of a potent DOTA-conjugated bombesin antagonist for targeting GRPr-positive tumors*, European J. of Nuclear Medicine and Molecular Imaging 38(1), 97-107 (2011), which is incorporated by reference with respect to such disclosure), other BBN derivatives, integrin-targeting peptides, Lupron sold by Takeda Abbott Pharmaceuticals, goserelin (Zoladex), buserelin (Bigonist), degarelix acetate (Firmagon), bortezomib (Velcade), edotreotide (Onalta), AMG 386 sold by Amgen, HER-2/neu vaccine sold by Corixa, pentetreotide (OctreoScan), depreotide trifluoroacetate (NeoTect), romidespin (Istodax), brentuximab vedotin (Adcetris) and other biological targeting peptide vectors, such as peptides that target diseases like cancer. Suitable exemplary antibodies are listed in Table 1, below. Additional exemplary antibodies include CC49. Additional exemplary targeting peptides and antibodies are disclosed in Li, N., *Synthesis and characterization of rhodium $^{105}$labeled thiamacrocycles for use to formulate peptide receptor agents* (1996) (Available from Dissertations & Theses @ University of Missouri—Columbia. (304275518)), Wong, S. and Jameson, D., Chemistry of Protein and Nucleic Acid Cross-Linking and Conjugation ($2^{nd}$ Ed.), CRC Press (2012), Wuts, P. and Greene, T., Greene's Protective Groups in Organic Synthesis ($4^{th}$ Ed.), John Wiley & Sons, Inc. (2007), Williams, P., et al., Chemical Approaches to the Synthesis of Peptides and Proteins, CRC Press (1997), Gross, E., and Meienhofer, J., The Peptides-Analysis, Synthesis, Biology ($1^{st}$ Ed.)(Vol. 1) Major Methods of Peptide Bond Formulation, Academic Press, Inc. (1979), Aime, S. et al., Ch. 19 *Chemistry of Molecular Imaging: An Overview*, Molecular Imaging: Principles and Practice (Weissleder, R., ed.), People's Medical Publishing House—USA (2010), Guillier, F., et al., *Linkers and Cleavage Strategies in Solid-Phase Organic Synthesis and Combinatorial Chemistry*, Chem. Rev., 100, 2091-2157 (2000), Albericio, A., et al., *Therapeutic Peptides*, Future Med. Chem. 4(12), 1527-1531 (2012) and Hamzeh-Mivehroud, M., et al., *Phage display as a technology delivering on the promise of peptide drug discovery*, Drug Discovery Today, 18(23/24), 1144-1157 (2013) which are incorporated by reference with respect to their disclosure of targeting vectors and their conjugation to other compounds. However any targeting vectors now known or hereafter developed that may be conjugated to the radioisotope trithiol complex of the present invention and are suitable for the intended use can be used consistent with the present invention.

TABLE 1

Antibody targeting vectors

| International non-proprietary name | Trade name | Target; Format | Indication first approved or reviewed |
|---|---|---|---|
| Alirocumab | (Pending) | PCSK9; Human IgG1 | High cholesterol |
| Mepolizumab | (Pending) | IL-5; Humanized IgG1 | Severe eosinophilic asthma |
| Necitumumab | (Pending) | EGFR; Human IgG1 | Non-small cell lung cancer |
| Nivolumab | Opdivo | PD1; Human IgG4 | Melanoma |
| Dinutuximab | (Pending) | GD2; Chimeric IgG1 | Neuroblastoma |
| Secukinumab | Cosentyx | IL-17a; Human IgG1 | Psoriasis |
| Evolocumab | (Pending) | PCSK9; Human IgG2 | High cholesterol |
| Blinatumomab | Blincyto | CD19, CD3; Murine bispecific tandem scFv | Acute lymphoblastic leukemia |
| Pembrolizumab | Keytruda | PD1; Humanized IgG4 | Melanoma |
| Ramucirumab | Cyramza | VEGFR2; Human IgG1 | Gastric cancer |
| Vedolizumab | Entyvio | α4β7 integrin; humanized IgG1 | Ulcerative colitis, Crohn disease |
| Siltuximab | Sylvant | IL-6; Chimeric IgG1 | Castleman disease |
| Obinutuzumab | Gazyva | CD20; Humanized IgG1; Glycoengineered | Chronic lymphocytic leukemia |

TABLE 1-continued

| Antibody targeting vectors | | | |
|---|---|---|---|
| International non-proprietary name | Trade name | Target; Format | Indication first approved or reviewed |
| Ado-trastuzumab emtansine | Kadcyla | HER2; humanized IgG1; immunoconjugate | Breast cancer |
| Raxibacumab | (Pending) | *B. anthrasis* PA; Human IgG1 | Anthrax infection |
| Pertuzumab | Perjeta | HER2; humanized IgG1 | Breast Cancer |
| Brentuximab vedotin | Adcetris | CD30; Chimeric IgG1; immunoconjugate | Hodgkin lymphoma, systemic anaplastic large cell lymphoma |
| Belimumab | Benlysta | BLyS; Human IgG1 | Systemic lupus erythematosus |
| Ipilimumab | Yervoy | CTLA-4; Human IgG1 | Metastatic melanoma |
| Denosumab | Prolia | RANK-L; Human IgG2 | Bone Loss |
| Tocilizumab | RoActemra, Actemra | IL6R; Humanized IgG1 | Rheumatoid arthritis |
| Ofatumumab | Arzerra | CD20; Human IgG1 | Chronic lymphocytic leukemia |
| Canakinumab | Ilaris | IL1b; Human IgG1 | Muckle-Wells syndrome |
| Golimumab | Simponi | TNF; Human IgG1 | Rheumatoid and psoriatic arthritis, ankylosing spondylitis |
| Ustekinumab | Stelara | IL12/23; Human IgG1 | Psoriasis |
| Certolizumab pegol | Cimzia | TNF; Humanized Fab, pegylated | Crohn disease |
| Catumaxomab | Removab | EPCAM/CD3;Rat/mouse bispecific mAb | Malignant ascites |
| Eculizumab | Soliris | C5; Humanized IgG2/4 | Paroxysmal nocturnal hemoglobinuria |
| Ranibizumab | Lucentis | VEGF; Humanized IgG1 Fab | Macular degeneration |
| Panitumumab | Vectibix | EGFR; Human IgG2 | Colorectal cancer |
| Natalizumab | Tysabri | a4 integrin; Humanized IgG4 | Multiple sclerosis |
| Bevacizumab | Avastin | VEGF; Humanized IgG1 | Colorectal cancer |
| Cetuximab | Erbitux | EGFR; Chimeric IgG1 | Colorectal cancer |
| Efalizumab | Raptiva | CD11a; Humanized IgG1 | Psoriasis |
| Omalizumab | Xolair | IgE; Humanized IgG1 | Asthma |
| Tositumomab-I131 | Bexxar | CD20; Murine IgG2a | Non-Hodgkin lymphoma |
| Ibritumomab tiuxetan | Zevalin | CD20; Murine IgG1 | Non-Hodgkin lymphoma |
| Adalimumab | Humira | TNF; Human IgG1 | Rheumatoid arthritis |
| Alemtuzumab | MabCampath, Campath-1H; Lemtrada | CD52; Humanized IgG1 | Chronic myeloid leukemia#; multiple sclerosis |
| Gemtuzumab ozogamicin | Mylotarg | CD33; Humanized IgG4 | Acute myeloid leukemia |
| Trastuzumab | Herceptin | HER2; Humanized IgG1 | Breast cancer |
| Infliximab | Remicade | TNF; Chimeric IgG1 | Crohn disease |
| Palivizumab | Synagis | RSV; Humanized IgG1 | Prevention of respiratory syncytial virus infection |
| Basiliximab | Simulect | IL2R; Chimeric IgG1 | Prevention of kidney transplant rejection |
| Daclizumab | Zenapax | IL2R; Humanized IgG1 | Prevention of kidney transplant rejection |
| Rituximab | MabThera, Rituxan | CD20; Chimeric IgG1 | Non-Hodgkin lymphoma |
| Abciximab | Reopro | GPIIb/IIIa; Chimeric IgG1 Fab | Prevention of blood clots in angioplasty |
| Muromonab-CD3 | Orthoclone Okt3 | CD3; Murine IgG2a | Reversal of kidney transplant rejection |

Certain non-limiting exemplary embodiments of the present invention include Formula II, Formula III and Formula IV as follows:

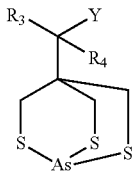

Formula II

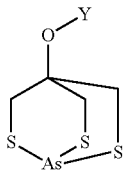

Formula III

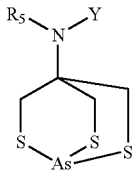

Formula IV wherein $R_3$, $R_4$ and $R_5$ may be separately selected from H, alkyl, or aryl of varying length and composition, and Y may be selected from various functional groups. Y may also comprise a spacer.

The present invention is also directed to methods for making the radioisotope trithiol complexes of the present invention. One exemplary method for making a radioisotope trithiol complex of the present invention comprises the step of reacting the radioisotope $^mM$ with a trithiol complex of Formula V:

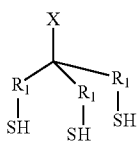

wherein $R_1$, and X are defined above.

Radioisotope $^mM$ will be present in the reaction mixture in radiotracer levels, which are generally micromolar or nanomolar concentrations. Levels of radioisotope in the reaction mixture may also be measured in ppm/ppb/ppt. The present invention can be used with radioisotope concentrations 20 µM or less, 15 µM or less, 10 µM or less, 5 µM or less, 1 µM or less, 900 nM or less, 600 nM or less, 300 nM or less and 100 nM or less, 50 nM or less, and all integers therebetween.

It will be understood that radioisotope concentrations are related to half-life of the radioisotope and to the volume of the reaction. The longer the half-life, the more atoms present and thus the higher the concentration. This is illustrated by the equation: $A=N\lambda$, with A=activity in disintegration per second (dps), N=# of atoms of radionuclide, and $\lambda=\ln 2$/half-life (in seconds).

The exemplary radioisotopes Arsenic-77 has a 38.8 h half-life and As-72 has a 28 h half-life, thus the concentration for the same activity will be higher for As-77. If 1.0 Curies (Ci) of As-77 in 1.0 mL of reaction volume are desired, then the concentration will be $1.24\times10^{-5}$ M or 12.4 µM. Many reactions according to the invention are on the microcurie to millicurie levels and thus the concentration will be lower. 1.0 Ci may be used for As-77 since it is a therapeutic radionuclide and the amount/activity administered to the patients will be higher. Typical imaging doses (ie, As-72) are likely to be in the range of 20-30 mCi or even less. The 20-30 mCi dose is in the range typically administered for Tc-99m (gamma emitter with a 6 h half-life). As-72 is a positron emitter and may require less.

At these radiotracer concentration levels, oxidation of the radioisotope is an issue, which impacts the nature of the solvents that can be used in the radiochemical reaction. Radioisotopes such as arsenic have different redox properties at the radiotracer level. There is also a potential for interference by low levels of impurities. The chemistry required to chelate the radioisotope at such concentration levels can be much different from that required when chelating a stable isotope at macroscopic levels. As a result, it is difficult to synthesize a stable radioisotope complex. Translation of macroscopic chemistry to the radiochemistry level is often not straightforward. It has been found that the trithiol complex of Formula V forms a stable radioisotope complex when combined with radiotracer levels of radioisotopes, such as radioisotopes of arsenic. The identity of the radioisotope trithiol complex was confirmed by RP-HPLC coupled to a radioisotope detector (as described in Example 1, below).

The radioisotope trithiol complex may be recovered from the reaction mixture by methods that will be readily understood by those of ordinary skill in the art, including filtration, extraction, Sep Pak, HPLC, or any combination thereof.

Because the no carrier added (NCA) concentrations of the starting material for the radioisotope trithiol complex are in the µM and nM range, to ensure that the reaction kinetics are sufficient, all other reactants are in large excess compared to the radioisotope concentration. A balance must be reached between minimizing the concentrations of the reactants and ensuring sufficiently fast kinetics of the radiolabeling reaction. It is particularly important to minimize the ligand (trithiol in this case) concentration when biological targeting molecules such as peptides are incorporated, which is the ultimate use of the ligand, since unlabeled and radiolabeled bioconjugate compete for available receptor sites.

In certain exemplary embodiments where the radioisotope is a radioisotope of arsenic, Arsenic-77 may be prepared by neutron irradiation of enriched $^{76}GeO2$. As-77 has a half-life of 38.9 h and emits a 1.65% abundant γ at 239 keV, as well as a 0.683 MeV β⁻ particle. Its parent, $^{77}Ge$, has a half-life of 11.3 h and emits the following gamma rays: 264.5, 215.6, and 211 keV in 52.6, 27.5, 28.1 percent abundance, as well as a 2.7 MeV β⁻ particle. Two exemplary methods for separating As-77 from Ge-77 are described in Jennewein, M. et al., *A new method for radiochemical separation of arsenic from irradiated germanium oxide*, Applied Radiation and Isotopes 63, 343-51 (2005) and Bokhari, T., et al., *Separation of no-carrier-added arsenic-77 from neutron irradiated germanium*, Radiochim. Acta, 97, 503-506 (2009).

The irradiated germanium dioxide target can be separated to provide $^{77}As$ as As(V) arsenate. The As(V) can then be reduced to tris(monothiol)arsine, an As (III) species. The reduction may be carried on in alcoholic or aqueous media. Reduction of the As(V) to As(III) can be performed by adding ethanol (an alcohol) and ammonium thioglycolate (a thiol) while heating. Other suitable reducing agents include other water soluble thiols, including monothiols. The resulting As(III) can then be directly added to the trithiol of Formula V to form the radioisotope trithiol complex of the present invention. NCA radioarsenic can be obtained as species other than As(V) and As(III), as discussed above with respect to $^m$M. Other radioarsenic isotopes may be produced from other germanium or arsenic targets.

Trithiols of Formula V can be formed by methods known to those skilled in the art and may include any of the chemical moieties and linking domains X discussed above. One suitable method can be derived from Ju, Y., et al., *Resisting Nucleophilic Substitution Reactions: Microwave-Assisted Synthesis of Azides, Thiocyanates in an Aqueous Medium*, J. of Organic Chemistry 71(17) 6697-6700 (2006), which is incorporated by reference for its disclosure of such methods.

In certain exemplary embodiments the hydroxyl groups of a trihyrdroxy compound are converted into good leaving groups, such as a tosylate, other sulfonyl groups or halide. The tosylated compound can be reacted with a nucleophile thiolating agent such as potassium thiocyanate or thioacetic acid to add the thiol groups. Unreduced groups, such as thiocyanate groups produced using potassium thiocyanate, may be reduced to form the thiol groups of Formula V. Suitable reducing agents include sodium borohydride, lithium aluminum hydride, dithiothreitol, tributyl tin hydride, or other thiols.

The functional group may be added at any suitable step before, during or after the synthesis of the trithiol portion of the compound. If the functional group is added before or during formation of the trithiol portion of the compound, reactants and reagents used in later steps will need to be selected to prevent destruction of the any functionality already present. For example, typically an ester-protecting group can be removed through saponification. However, in certain reaction schemes it may be desirable to avoid saponification due to the lability of the thiocyanate group in alkali base. Reagents, such as NHS and EDC may also be used to add functional groups. Exemplary processes for making certain exemplary compounds of Formula V, or compounds of Formula V protected with a thiocyanate group, are shown in FIGS. 2-7. The thiocyanate of the protected compound of Formula V is reduced to the thiol of Formula V before reacting with the radioisotope to produce a compound of Formula I. All exemplary processes may require additional steps to protect certain groups and prevent them from reacting, as could be readily understood by one of ordinary skill in the art.

The present invention is also directed to methods for using the radioisotope trithiol complex of the present invention. The radioisotope trithiol complex of the present invention is particularly well suited for radionuclear medicine applications, including imaging/diagnostic and therapeutic applications, such as chemotherapy. Other applications include use as a radiotracer in chemical or environmental applications, quantum dots that can be used in energy, semiconductor and solar applications, as well forming nanoparticles for various applications. The trithiol complex of Formula V can be used in separation applications to chelate nanomolar concentrations of radioisotopes from a mixture, for example by affixing the linking domain X of Formula V to a separation column.

Certain aspects of the invention are described with respect to the following non-limiting examples:

General

For both of Examples 1 and 2, the following reactants, reagents and methodologies were used.

Materials

Arsenic trioxide 1,1,1-tris(hydroxymethyl)propane, thioglycolic acid, pentaerythritol, triethyl orthoacetate, p-toluene sulfonyl chloride, p-toluene sulfonic acid monohydrate, propargyl bromide (80% in toluene), potassium thiocyanate, copper metal, copper sulfate pentahydrate, sodium ascorbate, sodium azide, ethyl 3-bromopropionoate, lithium aluminum hydride, anhydrous dimethylformamide, sodium chloride, sodium hydroxide, potassium carbonate, sodium bicarbonate, potassium hydroxide, ammonium chloride, triethyl amine, trifluroacetic acid, dioctyl phthalate, absolute ethanol, dichloromethane, ethyl acetate, anhydrous DMSO, tetrahydrofuran, pyridine, and ethyl ether were used. All reagents, solvents, acids and bases were reagent grade and used without further purification. Only 18 MΩ water was used. TWEEN® 80 (Sigma Aldrich-St. Louis, Mo.), silica gel 60 Å (Fisher Scientific-Pittsburgh, Pa.), silica gel TLC plates (SelectoScientific—Suwanee, Ga.), reversed phase C18 125 Å, aluminum backed C18-W TLC plates (Sorbtech—Norcross, Ga.), and 13 mm 0.2 µm Whatman nylon filter discs were available from commercial sources and used as received.

Arsenic-77 was prepared by neutron irradiation of 96.2% enriched $^{76}$GeO$_2$ purchased from Trace Sciences International (Richmond Hill, ON), in a thermal neutron flux of $2.4 \times 10^{14}$ n/cm$^2$-s at the University of Missouri Research Reactor (MURR). Arsenic-77: 38.9 h, 0.225 MeV $\beta_{-avg}$, 239 keV γ (1.65%); $^{77}$Ge: 11.3 h, 1.18 MeV $\beta_{-avg}$, several γ (211 keV (30%), 215.6 keV (27.9%), and 264.5 keV (53.3%)).

Physical Measurements.

$^1$H- and $^{13}$C-NMR spectra were obtained in CDCl$_3$ on a Bruker ARX-500 MHz spectrometer using TMS as an internal standard. Electrospray Ionization Mass Spectra (ESI-MS) were obtained on a Thermo Finnigan TSQ7000 triple-quadrupole instrument with an API2 source. Elemental analyses were performed by Atlantic Microlab, Inc. (Norcross, Ga.). An ORTEC HPGe detector outfitted with Genie multichannel analysis software was used to assay $^{77}$Ge and $^{77}$As liquid samples. Reversed phase HPLC (RP-HPLC) was performed using a Shimadzu Prominence HPLC system equipped with a pump, controller, and Prominence UV-Vis detector (model SPD20-AV) set to 254 nm, coupled to a Beckman 170 NaI(Tl) radioisotope detector. Reversed Phase HPLC was ran on a Thermo Scientific BetaBasic 18 (5 µm, 150 mm×4.6 mm) column was as follows: 3 minutes at 60/40 ACN/H$_2$O w/0.1% TFA, followed by a linear gradient to 75/25 over 7 min, and to 95/5 over 10 min, at a flow rate of 1 mL/min. An Eckert & Ziegler Bioscan AR-2000 Imager using LabLogic Win-Scan imaging scanner software (Version 2.2(11)) was used for scanning radioTLC plates.

X-ray Crystal Structures.

Figure 8:
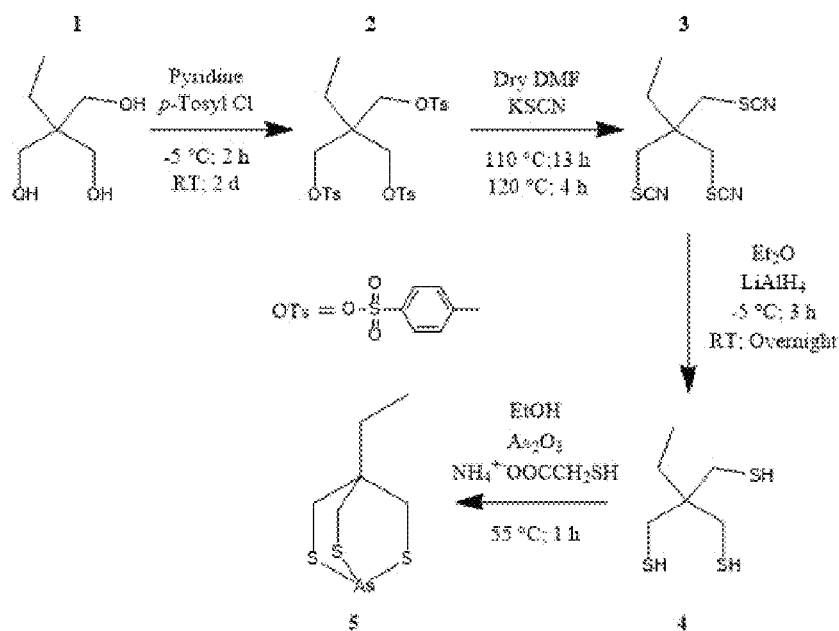
FIG. 8 depicts a reaction scheme for making an exemplary compound of Formula V and an arsenic trithiol complex.
Figure 12:
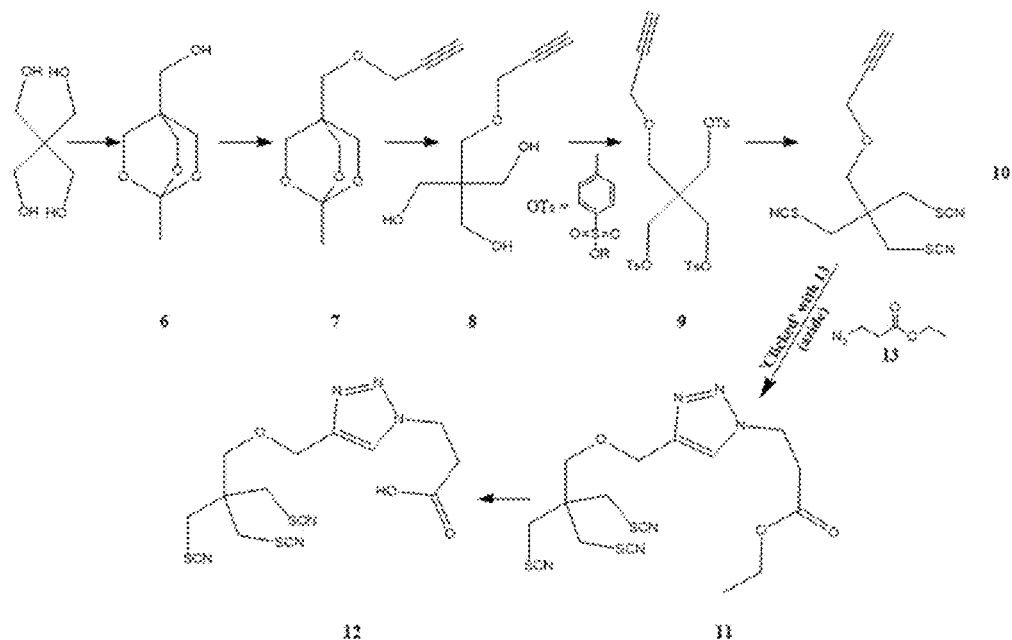
FIG. 12 depicts a reaction scheme for synthesizing an exemplary protected compound of Formula V.

Intensity data for compound 3, 5, 7, 10, and 12 in FIGS. 8 and 12 were obtained at −100° C. or −173° C. on a Bruker SMART CCD Area Detector system using the ω scan technique with Mo K α radiation from a graphite monochromator. Intensities were corrected for Lorentz and polarization effects. Equivalent reflections were merged, and absorption corrections were made using the multi-scan method. The structures were solved by direct methods with full-matrix least-squares refinement, using the SHELX package. All non-hydrogen atoms were refined with anisotropic thermal parameters. The hydrogen atoms were placed at calculated positions and included in the refinement using a riding model, with fixed isotropic U. Data were corrected for decay and absorption using the program SADABS. The final difference maps contained no features of chemical significance.

Example 1

Synthesis of Trithiol Complexes with Stable Arsenic and Radioisotopes of Arsenic A trithiol of Formula V, 4, was synthesized to evaluate its utility in stabilizing NCA$^{77}$As(III) on complexation. The trithiol, 4, was complexed with both stable arsenic to form Compound 5 and NCA $^{77}$As(III) to form Compound $^{77}$As-5. FIG. 8 is a schematic illustration of the synthesis for a trithiol of Formula V 4 and a trithioarsenic complex.

Using a modified literature procedure, compound 4 was prepared in an overall yield of 48% 2-Ethyl-2-((tosyloxy) methyl)propane-1,3-diyl bis(4-methylbenzenesulfonate), 2, was synthesized by reaction of 1,1,1-tris(hydroxymethyl) propane, 1, with excess p-toluene sulfonyl chloride in pyridine. Reaction of the tritosylate with excess potassium thiocyanate in dry DMF generated 1-thiocyanato-2,2-bis (thiocyanatomethyl)butane, 3. Prolonged heating at 120° C., or higher temperatures yielded unsatisfactory material and complicated the purification process. Reduction of compound 3 with lithium aluminum hydride in diethyl ether yielded 2-ethyl-2-(mercaptomethyl)propane-1,3-dithiol, 4. All intermediates and the final trithiol were purified using solvent extraction, recrystallization, and/or silica gel column chromatography. In some instances compound 5 was precipitated using water. The use of ammonium thioglycolate is not obvious, it was used to facilitate the dissolution of As$_2$O$_3$ in ethanol. Compound 5 was synthesized in an overall yield of 24%.

The synthesis process shown in FIG. 8 is described in more detail as follows:

2-Ethyl-2-((tosyloxy)methyl)propane-1,3-diyl bis(4-methylbenzenesulfonate) [C$_{27}$H$_{32}$O$_9$S$_3$], 2

1,1,1-Tris(hydroxymethyl)propane (1; 10.01 g, 74.6 mmol) was added to a stirring solution of pyridine (82.5 mL) at −5° C. p-Toluenesulfonyl chloride (71.04 g, 372.63 mmol) was then slowly added. After 2 hours the reaction was brought to room temperature and stirred for approximately 2 days. The reaction progress was followed by silica gel TLC with dichloromethane (DCM) as the mobile phase and visualized using UV-Vis, iodine, and KMnO$_4$ (ditosylate, R$_f$≈0.2; 2, R$_f$≈0.55; p-toluenesulfonyl chloride, Rf≈0.95). The reaction was poured into cold 2 M HCl (600 mL) to precipitate the crude product. The precipitate was washed with several portions of 2 M HCl (3×100 mL), dissolved into ethyl acetate (200 mL), and washed with 2 M HCl (1×50 mL), saturated sodium bicarbonate (3×100 mL), and brine (1×50 mL), dried over anhydrous MgSO$_4$, filtered, and taken to dryness under vacuum to give the product as a white solid. Yield: 42.94 g, 96.5%. $^1$H NMR (CDCl$_3$; 500 MHz) δ ppm: 0.64 (t, 3H, CH$_3$), 1.35 (q, 2H, CCH$_2$), 2.46 (s, 9H, ArCH$_3$), 3.77 (s, 6H, OCH$_2$), 7.36 (d, 6H, ArH), 7.71 (d, 6H, ArH). $^{13}$C NMR (CDCl$_3$ d$_6$; 125.8 MHz) δ ppm: 6.71 (CH$_3$), 21.72 (ArCH$_3$), 21.85 (CCH$_2$), 42.05 (C), 67.81 (OCH$_2$), 128.10 (ArC), 130.23 (ArC), 132.00 (ArC,) 145.52 (ArC). ESI-MS (m/z) 619.30 (619.08 calcd for [M+Na]$^+$ of [C$_{27}$H$_{32}$O$_9$S$_3$]). Elemental Anal. calc'd (found) for C$_{27}$H$_{32}$O$_9$S$_3$: C, 54.35 (54.40); H, 5.41 (5.47); S, 16.02 (16.12).

1-Thiocyanato-2,2-bis(thiocyanatomethyl)butane [C$_9$H$_{11}$N$_3$S$_3$], 3

Intermediate 2 (10.0 g, 16.8 mmol) and KSCN (21.2 g, 218.1 mmol) were added to dry DMF (50 mL) while vigorously stirring. The reaction mixture was heated to 110° C. for 13 h, and 4 h at 120° C., during which time solids formed and the reaction mixture turned dark brown. The reaction was monitored by silica gel TLC using DCM as the mobile phase, and visualized with UV-Vis, iodine, and KMnO$_4$ (3; R$_f$≈0.4). The reaction mixture was poured over crushed ice water (600 mL) and left in the freezer (−13° C.) overnight to precipitate the crude product 3. The brown precipitate was isolated by vacuum filtration, washed with deionized water, dissolved in EtOAc (200 mL), and dried over anhydrous Na$_2$SO$_4$. The solvent was removed by vacuum distillation to give brown oily crystalline product. Pure product was obtained by recrystallization from hot ethyl ether to yield 3 as a light yellow crystalline solid. X-ray quality crystals were grown by slow evaporation from chloroform. Yield: 2.6 g, 60.3%. $^1$H NMR (CDCl$_3$; 500 MHz) δ ppm: 1.01 (t, 3H, CH$_3$), 1.79 (q, 2H, CH$_2$), 3.25 (s, 6H, SCH$_2$). $^{13}$C NMR (CDCl$_3$; 125.8 MHz) δ ppm: 7.85 (CH3), 26.93(CCH$_2$), 38.50 (SCH$_2$), 44.78 (C), 111.18 (SCN). ESI-MS (m/z) 280.0 (280.08 calcd for [M+Na]$^+$ of [C$_9$H$_{11}$N$_3$S$_3$]). Elemental Anal. calc'd (found) for C$_9$H$_{11}$N$_3$S$_3$: C, 42.00 (42.78); H, 4.31 (4.47); N, 16.33 (15.61); S, 37.37 (36.95).

2-Ethyl-2-(mercaptomethyl)propane-1,3-dithiol [C$_6$H$_{14}$S$_3$], 4

Compound 3 was converted to the trithiol by reduction with lithium aluminum hydride. Under N$_2$, compound 3 (1.0 g, 3.9 mmol) and LiAlH$_4$ (0.89 g, 23.4 mmol) were added to a 50 mL three necked round bottom flask. After the reaction was cooled to −5° C., cold ethyl ether (30 mL) was added by syringe while stirring. The reaction continued stir for 3 h at −5° C., brought to room temperature and stirred overnight. Upon return, grey solids were present. The reaction was cooled then quenched by the slow addition of saturated ammonium chloride (20 mL). Solids were removed via vacuum filtration, and 2 M HCl (20 mL) was added to the mother liquor. The product, 4, was extracted into ethyl ether (3×50 mL), dried over anhydrous Na$_2$SO$_4$, filtered, and taken to dryness to yield a light yellow oil, which crystallized upon cooling. Yield: 584 mg, 82%. $^1$H NMR (CDCl$_3$; 500 MHz) δ ppm: 0.82 (t, 3H, CH$_3$), 1.18 (t, 3H, SH), 1.46 (q, 2H, CCH$_2$), 2.58 (d, 6H, SCH$_2$). $^{13}$C NMR (CDCl$_3$; 125.8 MHz) δ ppm: 7.85 (CH$_3$), 25.10 (CCH$_2$), 28.80 (SCH$_2$), 41.66 (C). ESI-MS (m/z) 181.12 (181.03 calcd for [M−H]$^-$ of [C$_6$H$_{14}$S$_3$]).

4-Ethyl-2,6,7-trithia-1-arsabicyclo[2.2.2]octane [C$_6$H$_{14}$S$_3$As], 5

Arsenic trioxide (0.101 g, 0.506 mmol) was dissolved in ethanol (95%, 20 mL) and ammonium thioglycolate (827.2 µL of 5.5 M aqueous solution, 4.55 mmol) were stirred vigorously while heating to 50° C. After 60 minutes 4 (0.184 g, 1.01 mmol) was added, stirring continued for 20 minutes, cooled, and then filtered to remove insoluble material. The filtrate was taken to dryness, washed with water (2×15 mL), dissolved in dichloromethane (10 mL), dried over anhydrous magnesium sulfate, filtered, and taken to dryness to yield light yellow crystals. X-ray quality crystals were grown by slow evaporation from chloroform. Yield: 0.135 g, 50.3%.

$^1$H NMR (CDCl$_3$; 500 MHz) δ ppm: 0.89 (t, 3H, CH$_3$), 1.39 (q, 2H, CH$_2$) 2.94 (s, 6H, SCH$_2$). $^{13}$C NMR (CDCl$_3$ d$_6$; 125.8 MHz) δ ppm: 8.17 (CH$_3$), 31.29 (C), 31.65 (SCH$_2$), 37.39 (CCH$_2$). ESI-MS (m/z) 254.69 (254.93 calcd for [M+H]$^+$ of [C$_6$H$_{11}$S$_3$As]). Elemental Anal. calc'd (found) for C$_6$H$_{11}$S$_3$As: C, 28.34 (31.42); H, 4.36 (4.70).

Radiotracer Synthesis of No-Carrier Added $^{77}$As-(4-ethyl-2,6,7-trithia-1-arsabicyclo[2.2.2]octane), $^{77}$As-5

No carrier added (NCA) $^{77}$As as arsenate in methanol was obtained from MURR. The solvent was removed by gentle heating (50° C.) under air flow, and the [$^{77}$As]arsenate (typically 3-5 mCi) was taken up in 1.0 mL of H$_2$O yielding a stock solution of 3-5 μCi/μL. The synthesis of $^{77}$As-5 was carried out by combining aqueous ammonium thioglycolate (500 mM), absolute EtOH, and 4 in absolute EtOH (55 mM) in a vial, adding [$^{77}$As]arsenate stock solution, capping and heating in a water bath. The total volume of the reaction was set at 500 μL and a solvent mixture of 90/10 EtOH/H$_2$O. The ammonium thioglycolate (10-25 mM final concentration), 4 (1 μM-1 mM final concentration), temperature (30-70° C.) and time (10-60 mM) were varied to optimize the radiolabeling yield. The radiolabeling yields were determined by silica gel TLC with ethyl ether as the mobile phase. The product, $^{77}$As-5, migrated with an Rf value of 0.88 while all other species ($^{77}$As-(thioglycolate)$_3$, $^{77}$As-arsenate/arsenite) remained at the origin.

Figure 9A:
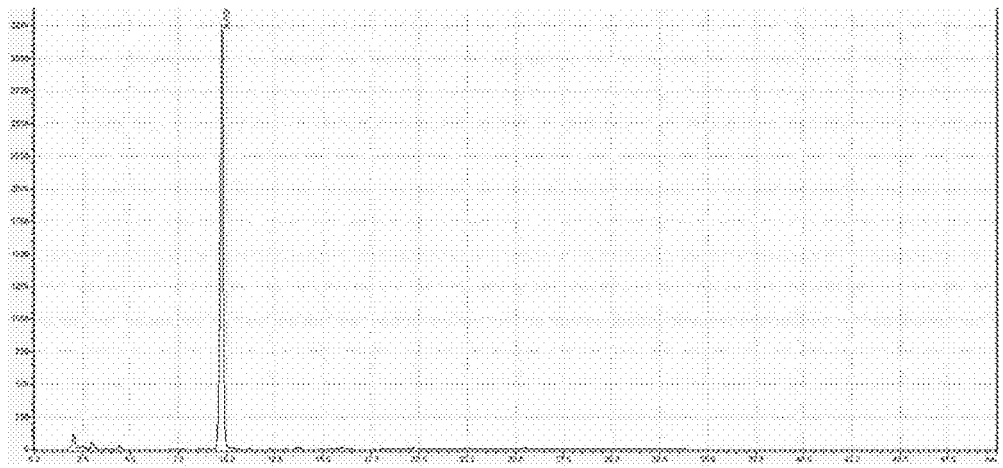
FIG. 9a is a UV-Vis HPLC chromatogram of arsenic trithiol complex 5 and FIG. 9b is the radioHPLC chromatogram of NCA radioarsenic trithiol complex $^{77}$As-5.
Figure 9B:
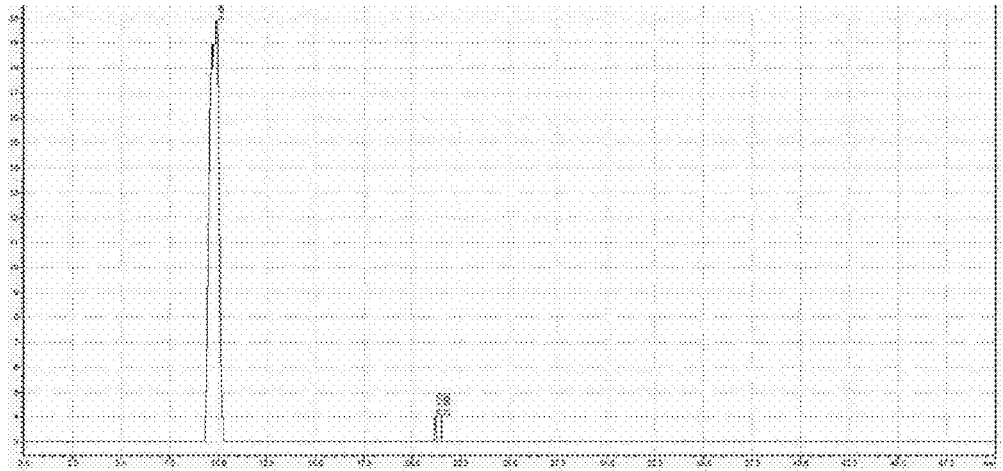

RP-HPLC revealed a radio peak for compound 5 with a retention time of 9.75 min as shown in FIG. 9a. The radiolabeling yield was determined by integration under the curve. As shown in FIG. 9b, it was determined that the peak at 9.88 min corresponded to a radiolabeling yield of 96%. The time difference of 0.13 min is attributed to the distance from the UV-Vis detector to the radiation detector. Unlabeled radioarsenic and $^{77}$GeO2 impurities would be located at the void (approx. 1 to 3-minutes).

Analysis

All compounds, 2-5, were characterized by elemental analysis, $^1$H- and $^{13}$C-NMR spectroscopy, and ESI-MS. $^1$H- and $^{13}$C-NMR data for compounds 4 and 5 are shown in Table 2. The molecular ions for all compounds were observed in the ESI-MS spectra at the calculated m/z values. The $^1$H-NMR spectra of the arsenic trithiol compound, 5, showed the disappearance of the —SH protons, a downfield shift of the methylene protons adjacent to the coordinated sulfur groups (SCH$_2$) and the methyl protons (CH$_3$). While an upfield shift in the methylene protons (CCH$_2$CH$_3$) of the bridgehead ethyl group relative to the free trithiol was observed. The $^{13}$C-NMR spectra of 5 showed downfield shifts for all except the bridgehead carbon, which was shifted upfield by ~10 ppm.

Single Crystal X-Ray Structures.

Figure 10:
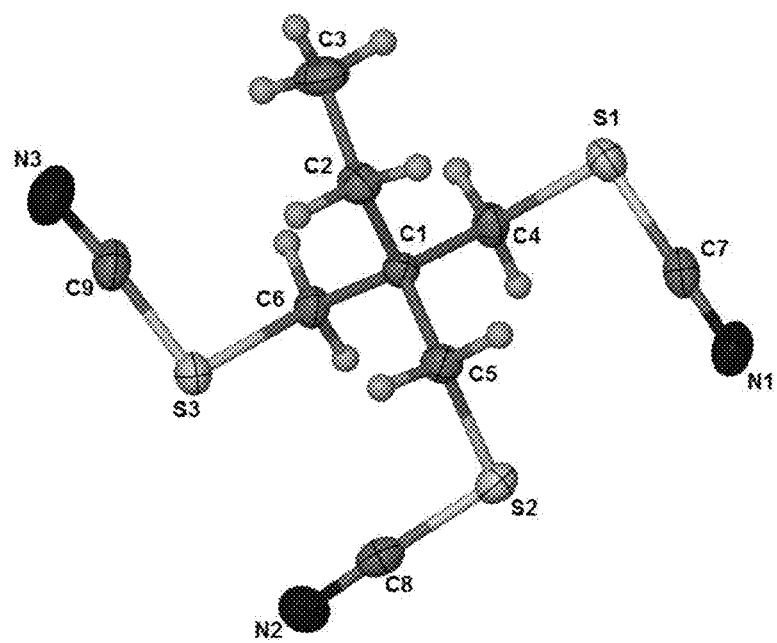
FIG. 10 shows the ORTEP structure of Compound 3.

Compounds 3 and 5 were characterized by single crystal X-ray diffraction analysis. Crystal refinement data, bond angles and distances are summarized in Tables 3 and 4. FIG. 10 shows the ORTEP structure of 3 with its three thiocyanate protecting groups. Bond distances and angles for compound 3 were in good agreement with previously reported organic thiocyanates. The average CN distance of 1.1464 Å calculated for C(7)N(1), C(8)N(3), and C(9)N(3) for 3 was within the range (1.139(2)-1.194(1) Å) previously reported for similar compounds. The average S—CN bond distance of 1.695 Å for S(1)C(7), S(2)C(8), and S(3)C(9) is in good agreement with previously reported distances of 1.63 Å to 1.693(2) Å. The average H$_2$C—SCN bond distance of 1.831 Å for S(1)C(4), S(2)C(5), and S(3)C(6), are slightly longer than previously reported (1.808(6) Å). The SCN angles observed lie within the range previously reported for organic thiocyanates of 172.3(1°) to 197.7(3°).

Figure 11:
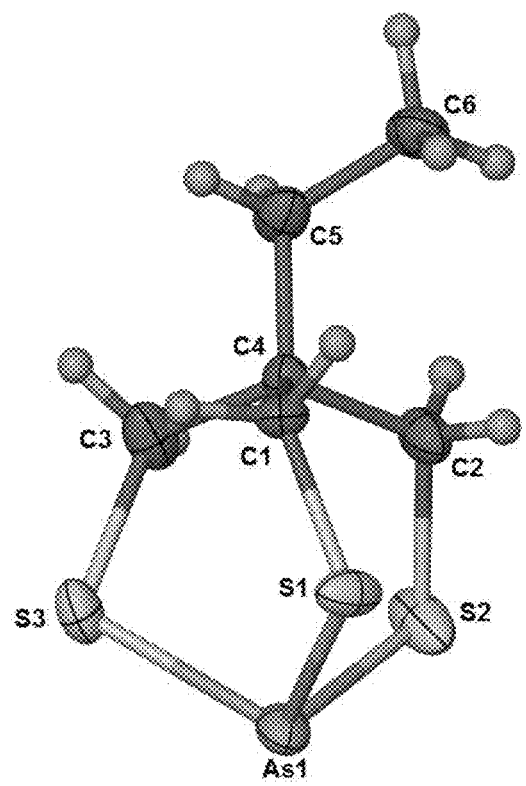
FIG. 11 shows the ORTEP structure of Compound 5.

The arsenic center in 5 exhibits the expected trigonal pyramidal geometry on coordination to trithiol 4 as shown in FIG. 11. The As—S bond distances observed (2.2348(7) A to 2.2379(8) Å) fall at the lower end of previously reported dithioarsine compounds (i.e., aryl-AsS$_2$ and X—AsS$_2$) containing 6-membered dithiolates. The S—As—S bond angles observed also fall at the low end of comparable arsine compounds previously reported (97.27(2°) to 102.20(5°).

TABLE 3

X-ray crystal Data, data collection parameters, and refinement parameters for 3 and 5.

| | 3<br>Trithiocyanate | 5<br>Arsenic Trithiol |
|---|---|---|
| Formula | C$_9$H$_{11}$N$_3$S$_3$ | C$_6$H$_{11}$AsS$_3$ |
| F.W. | 257.39 | 254.27 |
| Crystal System | Orthorhombic | Monoclinic |
| Space Group | P n a 21 | P 21/c |
| a (Å) | 17.766(5) | 11.153(3) |
| b (Å) | 9.957(3) | 11.486(3) |
| c (Å) | 6.913(2) | 7.2810(2) |
| α (°) | 90.00 | 90.00 |
| β (°) | 90.00 | 100.610(3) |
| γ (°) | 90.00 | 90.00 |
| V (Å$^3$) | 1222.8(6) | 916.8(4) |
| Z | 4.00 | 6.00 |
| r$_{calc}$, g/cm$^3$ | 1.40 | 1.86 |
| T, K | 173(2) | 173(2) |
| μ, mm$^{-1}$ | 0.58 | 4.10 |
| λ source (Å) | 0.71 | 0.71 |
| R(F) | 0.02 | 0.02 |

TABLE 2

$^1$H- and $^{13}$C-NMR data for 2-ethyl-2-(mercaptomethyl)propane-1,3-dithiol, 4, and 4-ethyl-2,6,7-trithia-1-arsabicyclo[2.2.2]octane, 5.

| | 4 | | | | 5 | | |
|---|---|---|---|---|---|---|---|
| $^1$H | ρ (ppm) | $^{13}$C | ρ (ppm) | $^1$H | ρ (ppm) | $^{13}$C | ρ (ppm) |
| CH$_3$ | 0.82 | CH$_3$ | 7.85 | CH$_3$ | 0.89 | CH$_3$ | 8.17 |
| SH | 1.18 | CCH$_2$ | 25.10 | | | CCH$_2$ | 37.39 |
| CCH$_2$ | 1.46 | SCH$_2$ | 28.80 | CCH$_2$ | 1.39 | SCH$_2$ | 31.65 |
| SCH$_2$ | 2.58 | C | 41.66 | SCH$_2$ | 2.94 | C | 31.29 |

TABLE 3-continued

X-ray crystal Data, data collection parameters, and refinement parameters for 3 and 5.

| | 3<br>Trithiocyanate | 5<br>Arsenic Trithiol |
|---|---|---|
| $R_w(F)^2$ | 0.06 | 0.05 |
| GoF | 1.07 | 1.03 |

$R = (\Sigma ||F_O| - |F_C||/\Sigma |F_O|)$.
$R_w = [\Sigma \bar{\omega}(|F_O^2| - |F_C^2|)^2/\Sigma \bar{\omega}(|F_O^2|^2]^{1/2}$.

TABLE 4

Selected bond angles (°) and distances (Å) for 3 and 5.

| 3<br>Trithiocyanate | | 5<br>Arsenic Trithiol | |
|---|---|---|---|
| S(1)—C(4) | 1.8317(2) | As(1)—S(1) | 2.2364(8) |
| S(1)—C(7) | 1.6932(2) | As(1)—S(2) | 2.2379(8) |
| S(2)—C(5) | 1.8332(1) | As(1)—S(3) | 2.2348(7) |
| S(2)—C(8) | 1.6977(2) | S(1)—C(1) | 1.826(2) |
| S(3)—C(6) | 1.8289(1) | S(2)—C(2) | 1.828(2) |
| S(3)—C(9) | 1.6935(2) | S(3)—C(3) | 1.832(2) |
| N(1)—C(7) | 1.1468(2) | C(1)—C(4) | 1.538(3) |
| N(2)—C(8) | 1.147(2) | C(2)—C(4) | 1.540(3) |
| N(3)—C(9) | 1.145(2) | C(3)—C(4) | 1.538(3) |
| C(1)—C(2) | 1.5505(2) | C(4)—C(5) | 1.551(3) |
| C(1)—C(4) | 1.5442(2) | C(5)—C(6) | 1.526(3) |
| C(1)—C(5) | 1.5376(2) | S(1)—As(1)—S(2) | 97.00(2) |
| C(1)—C(6) | 1.5410(2) | S(3)—As(1)—S(1) | 96.79(2) |
| C(2)—C(3) | 1.526(2) | S(3)—As(1)—S(2) | 96.82(3) |
| N(1)—C(7)—S(1) | 179.19(2) | C(1)—S(1)—As(1) | 101.91(7) |
| N(2)—C(8)—S(2) | 177.80(1) | C(2)—S(2)—As(1) | 101.73(7) |
| N(3)—C(9)—S(3) | 175.87(2) | C(3)—S(3)—As(1) | 101.18(8) |
| C(7)—S(1)—C(4) | 98.64(7) | C(4)—C(1)—S(1) | 116.82(1) |
| C(8)—S(2)—C(5) | 99.84(7) | C(4)—C(2)—S(2) | 116.80(2) |
| C(9)—S(3)—C(6) | 100.60(7) | C(4)—C(3)—S(3) | 117.71(2) |
| S(1)—C(4)—C(1) | 115.69(1) | C(2)—C(4)—C(1) | 111.94(2) |
| S(2)—C(6)—C(1) | 116.72(1) | C(3)—C(4)—C(1) | 111.08(2) |
| S(3)—C(8)—C(1) | 116.03(9) | C(3)—C(4)—C(2) | 111.52(2) |
| C(2)—C(1)—C(4) | 112.29(1) | C(1)—C(4)—C(5) | 107.84(2) |
| C(2)—C(1)—C(5) | 104.48(1) | C(2)—C(4)—C(5) | 108.50(2) |
| C(2)—C(1)—C(6) | 112.58(1) | C(3)—C(4)—C(5) | 105.65(2) |
| C(4)—C(1)—C(5) | 112.67(1) | C(4)—C(5)—C(6) | 116.80(2) |
| C(4)—C(1)—C(6) | 103.01(1) | | |
| C(5)—C(1)—C(6) | 112.09(1) | | |
| C(1)—C(2)—C(3) | 115.72(1) | | |

Example 2

Synthesis of Exemplary Radioarsenic Trithiol Complex

The synthesis of the trithiol precursors 3-(3-Thiocyanatomethyl) propoxy)prop-1-yne, 10, and 3-(4-((3-Thiocyanato-2,2-bis(thiocyanatomethyl)propoxy)methyl)-1H-1,2,3-triazol-1-yl)propanoic acid, 12, were prepared in 31%, and 15.2% yield, using modified literature procedures as shown in FIG. 12.

Compound 6 was synthesized by the reaction of pentaerythritol with triethyl orthoacetate in dioctyl phthalate containing trace p-toluene sulfonic acid monohydrate at 120° C. TEA or another trialkyl amine base is added prior to distillation of the product to react with the trace p-toluene sulfonic acid. If this step is omitted, the isolated compound will polymerize rapidly. Propargyl bromide can be reacted with the bicyclic orthoester, 6, in dry DMSO containing powdered KOH to yield the bicyclic orthoester alkyne, 7. Recrystallization from benzene or ethyl ether was possible, however typically the crude product was immediately added to a stirring solution of methanol containing 6 M HCl. Addition of base (solid $K_2CO_3$), at an appropriate time later, yielded compound 8 as a clear, light yellow oil. Tosylation of 8 was carried out using excess p-toluene sulfonyl chloride in pyridine to afford compound 9 in excellent yield. The 'clickable' trithiol precursor, 10, was synthesized by reacting the tritosylate with excess potassium thiocyanate in dry DMF at from 100° C. to 120° C.

Further reaction of ethyl 3-azidopropionate, 13, with the alkyne, 10, through a Huisgen 1,3-dipolar cycloaddition or 'click' reaction generated compound 11 in good yield. The ester protecting group was removed using an $H_2SO_4$ as an acid catalyst to afford 12 a linkable protected tridentate ligand of Formula V.

The Synthesis process shown in FIG. 12 is described in more detail as follows:

(1-Methyl-2,6,7-trioxabicyclo[2.2.2]octan-4-yl) methanol [$C_7H_{12}O_4$], 6

Pentaerythritol (60 g, 440.7 mmol) was added to a stirring solution of dioctyl phthalate (100 mL) containing trace p-toluene sulfonic acid monohydrate, and heated to 120° C. After triethyl orthoacetate (71.685 g, 81 mL, 441.87 mmol) was added in one portion the reaction was equipped with a distillation apparatus and stirred for 22 h. Upon return, 64 mL of ethanol had distilled (83% of the theoretical amount). TEA (40 drops) was added, stirred for 10 minutes, heated to 160° C. The TEA and remaining ethanol were removed under vacuum. After changing the distillation glassware, the final product, a white solid, was isolated by vacuum distillation at 185° C. and recrystallized using benzene. Yield: 83%, 58.64 g. $^1$H NMR (CDCl$_3$; 500 MHz) δ ppm: 1.453 (s, 3H, CH$_3$), 1.58 (t, 1H, OH), 3.454 (d, 2H, CCH$_2$OH), and 4.015 (s, 6H, OCH$_2$C). $^{13}$C NMR (CDCl$_3$; 125.8 MHz) δ ppm: 23.53 (CH$_3$), 35.71 (CH$_2$CCH$_2$), 61.50 (CCH$_2$OH), 69.41 (OCH$_2$C), and 108.67 (OCCH$_3$). ESI-MS (m/z): 161.06 (161.07 calc'd for $C_7H_{12}O_4$ [M+H]$^+$). Elemental analysis calc'd (found) for $C_7H_{12}O_4$: C, 52.49 (51.58); H, 7.55 (7.67).

1-Methyl-4-((prop-2-yn-1-yloxy)methyl)-2,6,7-trioxabicyclo[2.2.2]octane [$C_{10}H_{14}O_4$], 7

Compound 6 (5.434 g, 33.9 mmol) was added to a stirring solution of anhydrous DMSO (30 mL) and powdered KOH (7.6 g, 135.7 mmol). After stirring for 10 minutes, the reaction mixture was cooled in an ice bath (0° C.). Propargyl bromide (4.04 g, 3.02 mL, 33.93 mmol) was added dropwise, the reaction became dark brown rapidly. The reaction was stirred at room temperature for 95 minutes and poured into ice-cold water (200 mL). The product, an off-white solid, was collected by vacuum filtration, and washed with water, dried in vacuo to obtain the analytically pure product. X-ray quality crystals were obtained by slow evaporation from chloroform. Yield: 81%, 5.44 g. $^1$H NMR (CDCl$_3$; 500 MHz) δ ppm: 1.456 (s, 3H, CH$_3$), 2.442 (t, 1H, CCH), 3.286 (s, 2H, CCH$_2$O), 4.006 (s, 6H, (CH$_2$)$_3$C), and 4.094 (d, 2H, OCH$_2$CCH). $^{13}$C NMR (CDCl$_3$; 125.8 MHz) δ ppm: 23.56 (CH$_3$), 34.85 (CH$_2$CCH$_2$), 58.88 (OCH$_2$CCH), 68.12 (CCH$_2$O), 69.55 (OCH$_2$C), 75.34 (CH), 78.97 (CH$_2$CCH), 108.72 (OCCH$_3$). ESI-MS (m/z): 199.10 (199.09 calc'd for $C_{10}H_{14}O_4$ [M+H]$^+$). Elemental analysis calc'd (found) for $C_7H_{12}O_4$: C, 60.59 (59.06); H, 7.12 (7.23).

2-(Hydroxymethyl)-2-((prop-2-yn-1-yloxy)methyl) propane-1,3-diol [$C_8H_{14}O_4$], 8

Deprotection of 7 (2.225 g, 11.22 mmol) was accomplished by addition to 6 M HCl (12 mL) in methanol (40 mL)

at room temperature. After stirring for 16 h, potassium carbonate (5.6 g, 50 mmol) was added slowly and stirred for an additional 24 hours. The reaction was monitored by TLC using ethyl acetate as the mobile phase (8, $R_f$≈0.25), until no more starting material remained. Solvent was removed by vacuum distillation to give the crude product as a thick dark yellow oil. This crude mixture was dissolved into ethyl acetate, filtered, and taken to dryness to remove any solids (repeated several times). The crude product, a light yellow oil, was separated by silica gel column chromatography using ethyl acetate. Removal of the solvent under vacuum gave the pure product, a thick light yellow oil. Yield: 84%, 1.6 g. $^1$H NMR (CDCl$_3$; 500 MHz) δ ppm: 2.148 (bs, 3H, OH), 2.465 (t, 1H, CCH), 3.578 (s, 2H, CCH$_2$O), 3.722 (s, 6H, OCH$_2$C), and 4.154 (d, 2H, OCH$_2$CCH). $^{13}$C NMR (CDCl$_3$; 125.8 MHz) δ ppm: 45.14 (C), 58.98 (CCH$_2$O) 64.70 (HOCH$_2$C), 71.60 (OCH$_2$CCH), 79.40 (CH$_2$CCH), and 75.15 (CH). ESI-MS (m/z): 174.99 (175.09 calc'd for C$_8$H$_{14}$O$_4$ [M+H]$^+$)

2-((Prop-2-yn-1-yloxy)methyl)-2-((tosyloxy)methyl) propane-1,3-diyl bis(4-methylbenzenesulfonate) [C$_{29}$H$_{32}$O$_{10}$S$_3$], 9

Tosylation of 8 was accomplished by the slow addition of p-toluene sulfonyl chloride (78.76 g, 413.1 mmol) to a stirring solution of pyridine (90.3 g, 92 mL, 1.135 mol), and 8 (14.38 g, 82.56 mmol) at −5° C. The reaction was allowed to slowly warm to room temperature, and stirred for approximately 2 days. Reaction progress was followed by silica gel TLC using dichloromethane as the mobile phase and visualized with KMnO$_4$ (9, $R_f$≈0.55). The reaction was poured into cold 2 M HCl (400 mL) to give a thick white solid, which was washed with 2 M HCl (2×100 mL), and cold water (2×100 mL). The solid was dissolved into ethyl acetate (200 mL), and washed with 2 M HCl (2×100 mL), saturated sodium bicarbonate (2×50 mL), and brine (1×50 mL). The organic layer was dried over magnesium sulfate, filtered, and taken to dryness to give the crude product as a clear light yellow oil. Purification was accomplished though the dissolution of the crude product in a mixture of hot hexane/DCM (70/30) followed by the removal of DCM in vacuo. Hot hexanes were decanted from the solids present. This process was repeated to the solid product until the hexane revealed no more UV active material. The solids were taken to dryness under vacuum to give the product as a white solid. Yield: 92%, 48.21 g. $^1$H NMR (CDCl$_3$; 500 MHz) δ ppm: 2.408 (t, 1H, CH), 2.468 (s, 9H, CH$_3$), 3.358 (s, 2H, CCH$_2$O), 3.890 (m, 8H, OCH$_2$CCH and OCH$_2$C), 7.357 (d, 6H, ArH), and 7.716 (d, 6H, ArH). $^{13}$C NMR (CDCl$_3$; 125.8 MHz) δ ppm: 21.87 (CH$_3$), 43.76 (CH$_2$CCH$_2$), 66.11 (OCH$_2$CCH), 66.89 (OCH$_2$C), 75.51 (CH), 78.66 (CH$_2$CCH), 128.16 (ArC), 130.22 (ArC), 132.01 (ArC), and 145.50 (ArC). Elemental analysis calc'd (found) for C$_{29}$H$_{32}$O$_{10}$S$_3$: C, 54.70 (54.48); H, 5.07 (5.12); S, 15.10 (15.01).

3-(3-Thiocyanatomethyl)propoxy)prop-1-yne [C$_{11}$H$_{11}$N$_3$OS$_3$], 10

To a 100 mL round bottom flask equipped with a condenser, 9 (10.02 g, 15.75 mmol), and KSCN (19.86 g, 204.8 mmol) in anhydrous DMF (70 mL) were heated to 110° C. for 18 hours, 120° C. for 2 hours, and an additional 8 hours at 110° C. while vigorously stirring under nitrogen. The reaction was monitored by TLC using DCM as the mobile phase and visualized with I$_2$, UV, and KMnO$_4$ until no more starting material remained (10, $R_f$≈0.4). The dark brown reaction mixture was poured over crushed ice water (800 mL) and left in the overnight in the freezer (−13° C.) overnight to precipitate the crude product as dark brown solid. The solids were collected by vacuum filtration, dissolved in ethyl acetate, passed through a plug of silica using ethyl acetate (200 mL), and taken to dryness. Pure product, a light yellow precipitate, was obtained by recrystallization from hot ethyl ether. Yield: 2.79 g, 60%. $^1$H NMR (CDCl$_3$; 500 MHz) δ ppm: 2.53 (t, 1H, CH), 3.33 (s, 6H, OCH$_2$C), 3.70 (s, 2H, CCH$_2$O), and 4.24 (d, 2H, OCH$_2$CCH). $^{13}$C NMR (CDCl$_3$; 125.8 MHz) δ ppm: 37.04 (SCH$_2$C), 46.17 (CH$_2$CCH$_2$), 58.69 (CCH$_2$O), 68.97 (OCH$_2$CCH), 76.42 (CH), 78.09 (CH$_2$CCH), and 111.53 (SCN). Elemental analysis calc'd (found) for C$_{11}$H$_{11}$N$_3$OS$_3$: C, 44.42 (44.72); H, 3.73 (3.67); N, 14.13 (13.86); S, 32.34 (32.51).

Ethyl 3-(4-((3-thiocyanato-2,2-bis(thiocyanatomethyl)propoxy)methyl)-1H-1,2,3-triazol-1-yl)propanoate [C$_{16}$H$_{20}$N$_6$O$_3$S$_3$], 11

10 (1.19 g, 4 mmol) and 13 (1.76 g, 12 mmol) were added to a stirring solution of copper (II) sulfate pentahydrate (21.9 mg, 0.08 mmol), sodium ascorbate (270 mg, 1.2 mmol), copper metal (1 g), THF (4 mL), ACN (4 mL), H$_2$O (4 mL), and t-BuOH(4 mL) at 55° C. The reaction was monitored by silica gel TLC using DCM as a mobile phase and visualized with I$_2$, UV, and KMnO$_4$. Once the starting material had been consumed, 10, the solvents were removed by vacuum distillation. The crude product was dissolved into DCM and added to a plug of silica. DCM (100 mL) was added to remove unwanted materials. Ethyl acetate (250 mL) was used to obtain the crude compound of interest 11. Further purification was accomplished by silica gel column chromatography (3×18 cm, 40 g) using 40/60 hexanes/ethyl acetate to 20/80 hexanes/ethyl acetate to 100% ethyl acetate to obtain the compound of interest as a clear light yellow oil. Yield: 1.73 g, 98%. $^1$H NMR (CDCl$_3$; 500 MHz) δ ppm: 1.24 (t, 3H, CH$_3$), 2.96 (t, 2H, CH$_2$C00), 3.28 (s, 6H, NCSCH$_2$), 3.65 (s, 2H, CCH$_2$), 4.15 (q, 2H, COOCH$_2$), 4.64 (t, 2H, NCH$_2$), 4.67 (s, 2H, OCH$_2$C=C), and 7.71 (s, 1H, CH). $^{13}$C NMR (CDCl$_3$; 125.8 MHz) δ ppm: 14.22 (CH$_3$), 34.64 (CH$_2$COO), 36.92(NCSCH$_2$), 45.74 (NCH$_2$), 46.08 (C), 61.36 (COOCH$_2$), 64.18 (CCH$_2$O), 69.33 (OCH$_2$), 111.62 (SCN), 124.64 (C=C), 143.11 (C=C), and 170.53 (C=0).

3-(4-((3-Thiocyanato-2,2-bis(thiocyanatomethyl) propoxy)methyl)-1H-1,2,3-triazol-1-yl)propanoic acid [C$_{14}$H$_{16}$N$_6$O$_3$S$_3$], 12

Concentrated sulfuric acid (10 drops) was added to stirring solution of compound 11 (0.40 g, 0.908 mmol) in ACN (5 mL) and water (25 mL) at 70° C. The reaction was refluxed, and monitored until by silica gel TLC using a 20/80 mix of hexane/ethyl acetate as a mobile phase (13, $R_f$≈1; 11, $R_f$≈0.5; 12, $R_f$≈0.25). ACN was removed via vacuum distillation, and the remaining material was extracted into DCM (3×50 mL). Organic layers were combined, dried over anhydrous sodium sulfate, filtered, and taken to dryness. The analytically pure product was obtained from reverse phase C18 column (3×15 cm) using 40/60 ACN/H$_2$O as a mobile phase (12, $R_f$≈0.6 by reversed phase TLC using 40/60 ACN/H$_2$O as a mobile phase). Solvent was removed in vacuo to afford a light yellow oil. X-ray quality crystals were obtained by slow evaporation of the column fractions. Yield: 50%, 0.187 g. $^1$H NMR (CDCl$_3$; 500 MHz) δ ppm: 3.03 (t, 2H, CH$_2$COO), 3.29 (s, 6H, NCSCH$_2$), 3.64 (s, 2H, CCH$_2$), 4.65 (t, 2H, NCH$_2$), 4.67 (s, 2H, OCH$_2$C≡C), and 7.76 (s, 1H, CH). $^{13}$C NMR (CDCl$_3$; 125.8 MHz) δ ppm: 34.34 (CH$_2$COO), 36.95 (NCSCH$_2$), 45.79 (NCH$_2$), 46.05 (C), 63.94 (CCH$_2$O), 69.38 (OCH$_2$), 111.77 (SCN), 124.95 (C═C), 143.07 (C═C), and 173.92 (C═O).

Figure 13:
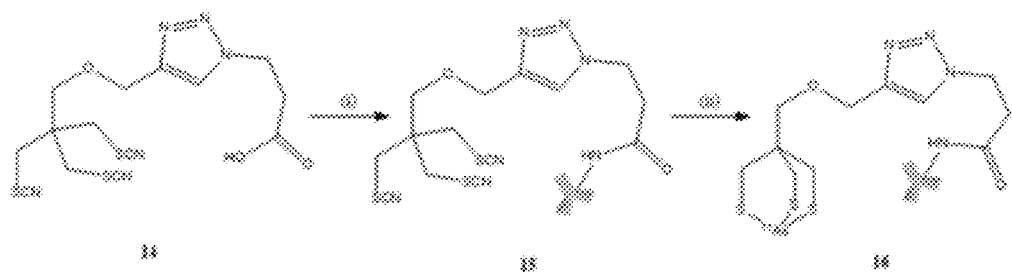
FIG. 13 depicts a proposed reaction scheme for converting a compound produced in the reaction scheme of FIG. 12 into an exemplary radioarsenic trithiol complex of the invention.

A proposed method for conjugating compound 12 to an antibody targeting vector and linked to a radioisotope of arsenic is shown in FIG. 13. A suitable reaction scheme can be derived from that disclosed in Mohsin, H., et al., *Radio-lanthanide-labeled Monoclonal Antibody CC49 for Radioimmunotherapy of Cancer: Biological Comparison of DOTA Conjugates and $^{149}$Pm, $^{166}$Ho, and $^{177}$Lu*, Bioconjugate Chem., 17, 485-492 (2006), as follows: An aliquot of CC49 is conjugated with the bifunctional chelating agent N-hydroxy-sulfosuccinimidyl DOTA (DOTA-OSSu) at a 20:1 molar ratio of DOTA-OSSu:mAb. A solution DOTA in H$_2$O is adjusted to pH 5.45 with 1 M NaOH and cooled to 4° C. To a portion of the DOTA solution freshly prepared (at 4° C.) sulfo-NHS is added. Then EDC, freshly prepared in H$_2$O is added, and the reaction mixture is stirred at 4° C. for 30 min. Prior to being added to the mAb, the pH of the reaction mixture is adjusted to 7.3 with 40 μL of 0.2M Na2HPO4, pH 9.2.

The mAb may be labelled using the following general procedure: An aliquot of CC49 in 1 mL of 10 mM NaH$_2$PO$_4$/150 mM NaCl, pH 7.4, is dialyzed against 1 L of 0.1M Na2HPO4, pH 7.5, containing approximately 1 g of Chelex 100, for 18 to 24 h at 4° C., and then against 1 L of 0.1M NaHCO$_3$/Na$_2$HPO$_4$, pH 8.5, containing approximately 1 g of Chelex 100, for 48 h at 4° C., with one buffer change. The DOTA-CC49 conjugate concentrations is measured by absorbance at 280 nm. The average number of chelates per antibody is determined using an 111In isotopic dilution assay method previously published by Lewis, M., et al., *An improved method for conjugating monoclonal antibodies with N-hydroxysulfosuccinimidyl DOTA*, Bioconjugate Chem, 12, 320-324 (2001).

Analysis

The key intermediates, 6, 9, 10, and 12, were characterized by elemental analysis, while all compounds were characterized by $^1$H- and $^{13}$C-NMR spectroscopy, and ESI-MS. The molecular ions for all compounds were observed in the ESI-MS spectra at the calculated m/z values. Elemental analysis of the compounds were in line with their calculated values.

Alkyne bearing compounds 7-10 exhibited long range coupling of the $^1$H chemical shifts for the methylene group adjacent to the C≡CH group at 3.89-4.24 ppm to the terminal proton (C≡CH) at 2.41-2.53 ppm. $^{13}$C chemical shifts of this functional group fell between 78.09-79.40 ppm (C≡CH) and 75.34-76.42 ppm (C≡CH). REF Thiocyanate bearing compounds 10-12, exhibited $^{13}$C-NMR shifts from 111.52-111.77 ppm. REF Compounds 11 was easily identified by the disappearance of the alkyne $^1$H- and $^{13}$C-NMR signals, mentioned above, and appearance of a $^1$H NMR signal found at 7.71 ppm (C═CHN) and $^{13}$C-NMR signals at 124.64 ppm (C═CHN), and 143.11 ppm (C═CHN) for the proton and carbons located within the triazole ring. Similar chemical shifts at 7.76 ppm ($^1$H for C═CHN) and 124.95 ppm ($^{13}$C for (C═CHN)) and 143.07 ppm (13C for (C═CHN)) were observed for compound 12. REF The $^1$H- and $^{13}$C-NMR spectra of the compounds reported, 6-13, were characteristic of the functional groups present and comparable to available literature.

Single Crystal X-Ray Structures

Figure 14:
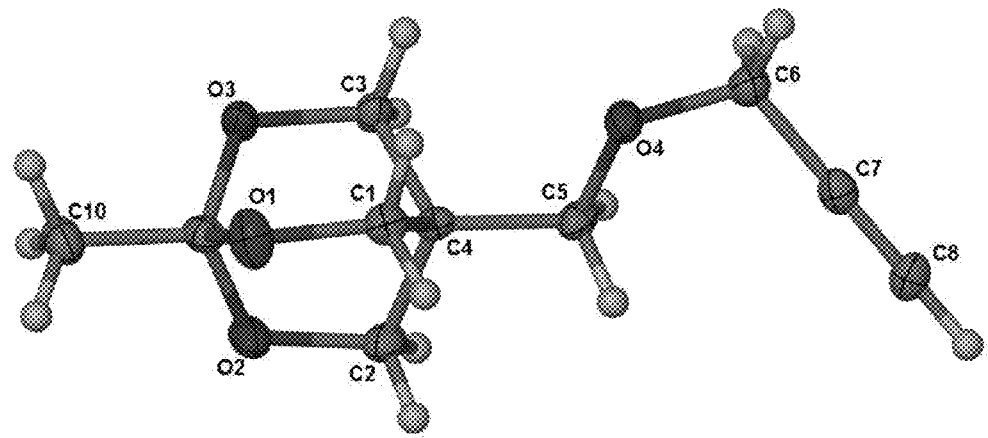
FIG. 14 shows the ORTEP structure of compound 7.
Figure 15:
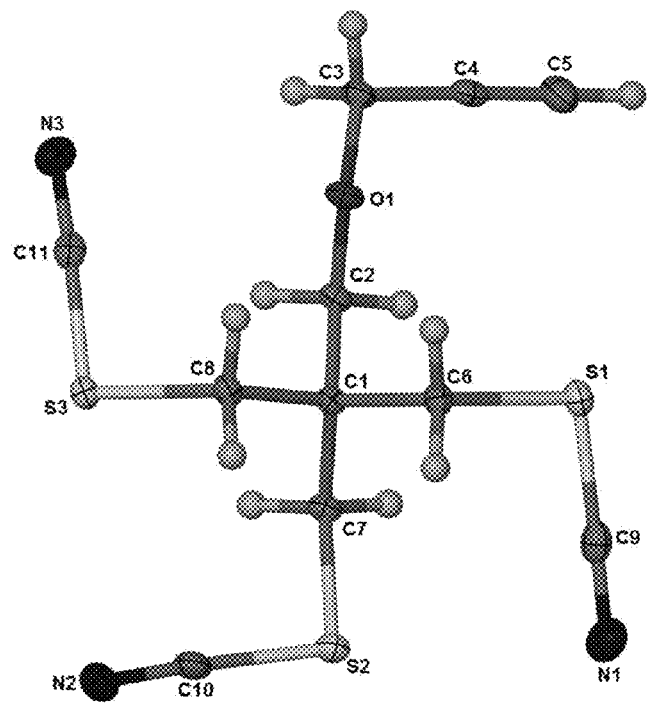
FIG. 15 shows the ORTEP structure of compound 10.
Figure 16:
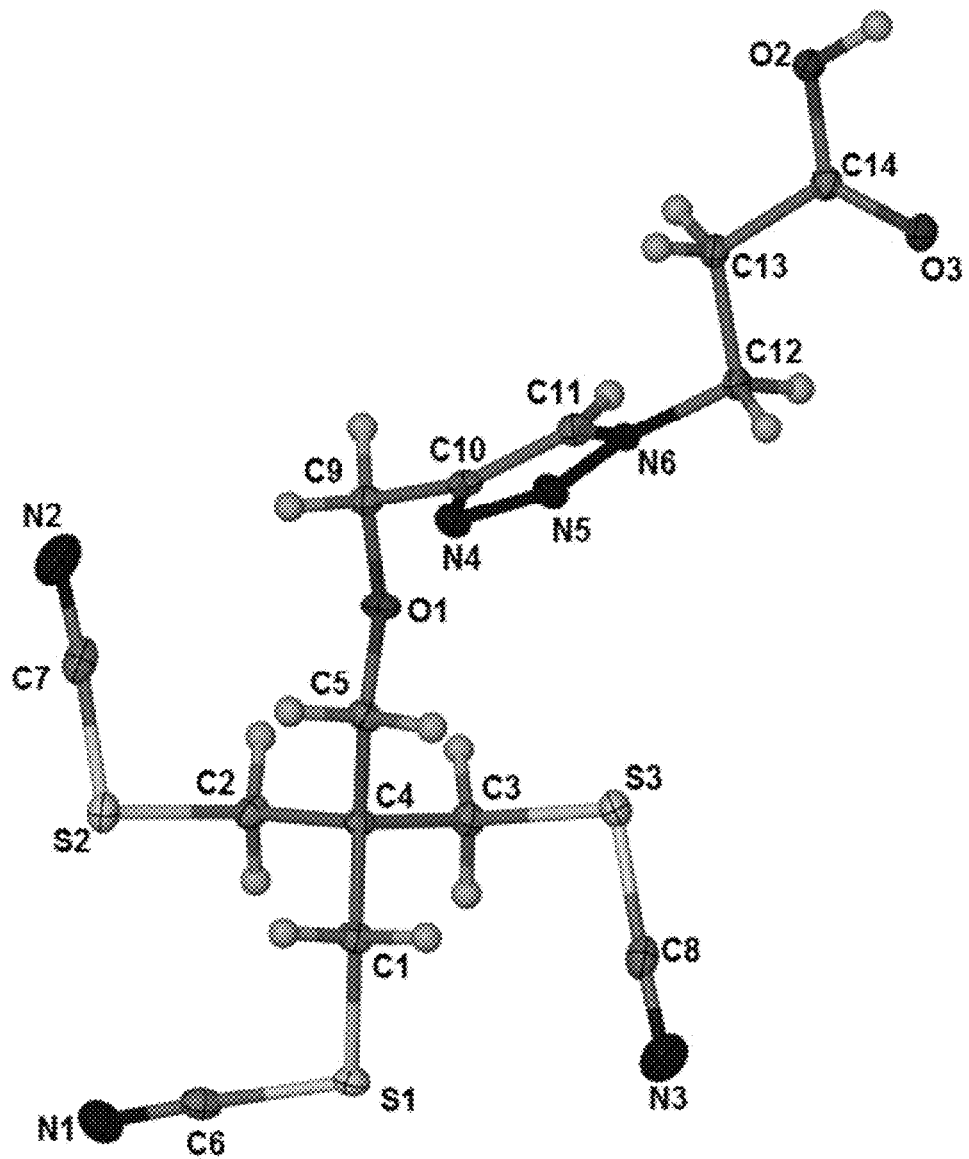
FIG. 16 shows the ORTEP structure of compound 12.

Compounds 7, 10, and 12 were characterized by single crystal X-ray diffraction analysis. Crystal refinement data, bond angles, and distances are summarized in Tables 5 and 6. FIG. 14 shows the ORTEP structure of 7 with an alkyne functional group attached to the protected bicyclic orthoester while FIGS. 15 & 16 show ORTEP structures for the alkyne and carboxylic acid linkable trithiocyanate compounds. Bond distances and angles for compounds 10 and 12 were in agreement with the literature. The average C—N distance of compounds 10 and 12, was 1.1472 Å and 1.1466 Å, respectively. This falls within the range of previously reported organic mono-thiocyanate compounds (1.139(2)-1.194(1) Å) and is in good agreement with another trithiocyanate previously reported in section 2.6.1 of this chapter (1.1464 Å). The average S—CN distance 1.6982 Å and 1.6955 Å reported here are slightly longer than similarly reported compounds (1.63 Å to 1.693(2) Å), however are in excellent agreement with our previously reported trithiocyanates (Average of 1.695 Å and range of 1.6932(2) Å to 1.6977(2) Å). The adjacent methylene, CH$_2$—SCN reported here have an average bond distance of 1.8332 Å, and 1.8303, respectively. Again, these are slightly longer than previously reported compounds but in agreement with the distances reported for our trithiocyanate. The SCN angles reported here (176.4(2°) to 179.12(14)°) lie within the range of previously reported organic thiocyanates (172.3(1°) to 179.7(3)°).

TABLE 5

X-ray crystal Data, data collection parameters, and refinement parameters for 7, 10, and 12.

| | 7<br>Bicyclic<br>Orthoester | 10<br>Alkyne<br>Trithiocyanate | 12<br>Trithiocyanate<br>COOH |
|---|---|---|---|
| Formula | C$_{10}$H$_{14}$O$_4$ | C$_{11}$H$_{11}$NOS$_3$ | C$_{14}$H$_{18}$N$_6$O$_4$S$_3$ |
| F.W. | 198.21 | 297.41 | 430.52 |
| Crystal System | Monoclinic | Triclinic | Monoclinic |
| Space Group | P 21/c | P-1 | P 21/c |
| a (Å) | 7.9189(2) | 7.4212(9) | 12.3916(4) |
| b (Å) | 18.4612(5) | 9.2485(12) | 9.8148(3) |
| c (Å) | 6.8206(2) | 10.4614(13) | 16.0906(5) |
| α (°) | 90 | 76.4950(10) | 90 |
| β (°) | 103.7190(1) | 85.795(2) | 101.410(2) |
| γ (°) | 90 | 78.1660(10) | 90 |
| V (Å$^3$) | 968.67(5) | 683.08(15) | 1918.28(10) |
| Z | 4 | 2 | 4 |
| r$_{calc}$, g/cm$^3$ | 1.359 | 1.446 | 1.491 |
| T, K | 173(2) | 100(2) | 100(2) |
| μ, mm$^{-1}$ | 0.877 | 0.533 | 0.42 |
| λ source (Å) | 1.54178 | 0.71073 | 0.7173 |
| R(F) | 0.0355 | 0.0252 | 0.0375 |
| R$_w$(F)$^2$ | 0.0881 | 0.0646 | 0.076 |
| GoF | 1.101 | 1.065 | 1.02 |

$R = (Σ \mid\mid F_O \mid - \mid F_C \mid\mid / Σ \mid F_O \mid)$.
$R_w = [Σ\overline{\omega}(\mid F_O^2 \mid - \mid F_C^2 \mid)^2 / Σ\overline{\omega}(\mid F_O^2 \mid)^2]^{1/2}$

TABLE 6

Selected bond angles (°) and distances (Å) for 7, 10, and 12.

| 7<br>Bicyclic<br>Orthoester | | 10<br>Alkyne<br>Trithiocyanate | | 12<br>Trithiocyanate<br>COOH | |
|---|---|---|---|---|---|
| O(1)—C(9) | 1.4082(1) | C(1)—C(8) | 1.5454(18) | S(1)—C(1) | 1.834(2) |
| O(1)—C(1) | 1.4409(1) | C(3)—C(4) | 1.472(2) | S(2)—C(2) | 1.830(2) |
| O(2)—C(9) | 1.4067(1) | C(4)—C(5) | 1.185(2) | S(3)—C(3) | 1.827(2) |
| O(2)—C(2) | 1.4351(1) | S(1)—C(6) | 1.8321(14) | S(1)—C(6) | 1.696(2) |
| O(3)—C(9) | 1.4046(1) | S(2)—C(7) | 1.8302(14) | S(2)—C(7) | 1.693(2) |
| O(3)—C(3) | 1.4357(1) | S(3)—C(8) | 1.8374(14) | S(3)—C(8) | 1.697(2) |
| O(4)—C(6) | 1.4228(1) | S(1)—C(9) | 1.6958(16) | N(1)—C(6) | 1.142(3) |
| O(4)—C(5) | 1.4279(1) | S(2)—C(10) | 1.6985(16) | N(2)—C(7) | 1.149(3) |
| C(1)—C(4) | 1.5224(2) | S(3)—C(11) | 1.7004(16) | N(3)—C(8) | 1.148(3) |
| C(2)—C(4) | 1.5263(2) | N(1)—C(9) | 1.147(2) | N(1)—C(6)—S(1) | 178.3(2) |
| C(3)—C(4) | 1.5236(1) | N(2)—C(10) | 1.146(2) | N(2)—C(7)—S(2) | 176.4(2) |
| C(4)—C(5) | 1.5130(2) | N(3)—C(11) | 1.148(2) | N(3)—C(8)—S(3) | 177.9(2) |
| C(6)—C(7) | 1.4684(2) | C(5)—C(4)—C(3) | 178.25(16) | | |
| C(7)—C(8) | 1.1858(2) | N(1)—C(9)—S(1) | 179.12(14) | | |
| C(9)—C(10) | 1.4966(2) | N(2)—C(10)—S(2) | 176.55(14) | | |
| C(9)—O(1)—C(1) | 112.41(9) | N(3)—C(11)—S(3) | 176.85(14) | | |
| C(9)—O(2)—C(2) | 112.40(8) | | | | |
| C(9)—O(3)—C(3) | 112.18(8) | | | | |
| C(6)—O(4)—C(5) | 112.82(8) | | | | |
| O(1)—C(1)—C(4) | 108.38(9) | | | | |
| O(2)—C(2)—C(4) | 108.59(9) | | | | |
| O(3)—C(3)—C(4) | 108.89(9) | | | | |

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A radioisotope trithiol complex according to Formula I:

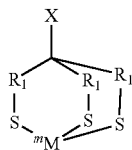

wherein each $R_1$ is independently $C_1$ to $C_5$ substituted or unsubstituted hydrocarbyl;
$^mM$ is a radioisotope; and
X is a chemical moiety.

2. The complex of claim 1, which X is a linking domain comprising a functional group.

3. The complex of claim 2, wherein said functional group is selected from the group consisting of phosphonic acid, isothiocyanate, maleimide, carboxylic acid, primary amine, aldehyde, sulfonyl chloride, secondary amine, hydroxide, aryl-NCS, alkene, alkyne, azide, active esters, thiol, $CH_2OH$, $CH_2OCH_3$, $CH_2OCOCH_3$, $COOC_2H_5$, $CONHC_3H_7$, CO-Phe-$OC_2H_5$, CO-Phe-OH, CO-Phe-Ala-OH, CO-Phe-Met-$OCH_3$, and CO-Phe-Phe-Gly-Leu-Met-$NH_2$.

4. The complex of claim 2, further comprising a targeting vector conjugated to the linking domain.

5. The complex of claim 4, wherein the targeting vector is selected from the group consisting of peptides, antibodies, oligonucleotides, carbohydrates, lipids, and organic molecules.

6. The complex of claim 5, wherein the targeting vector is selected from the group consisting of peptides and antibodies.

7. The complex of claim 2, wherein linking domain X comprises a spacer.

8. The complex of claim 1, wherein $^mM$ is selected from the group consisting of a radioisotope of arsenic, lead, mercury, silver, copper, platinum, lanthanides, actinides, rhenium, nickel, bismuth, technetium, gallium, rhodium and zinc.

9. The complex of claim 8, wherein $^mM$ is a radioisotope of arsenic.

10. The complex of claim 1, wherein each $R_1$ has the same number of carbon atoms.

11. The complex of claim 10, wherein each $R_1$ is a methyl group.

12. A method for making the radioisotope trithiol complex of claim 1, comprising:
reacting the radioisotope $^mM$ with a trithiol complex of Formula V:

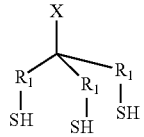

wherein X and $R_1$ are defined as in claim 1.

13. The method of claim 12, wherein $^mM$ is a radioisotope of arsenic.

14. The method of claim 12, wherein the radioisotope is present in a concentration lower than 20 μM.

15. A method of using the radioisotope trithiol complex of claim 1 in nuclear medicine.

16. A radioisotope trithiol complex according to Formula I:

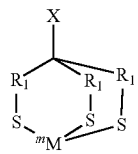

wherein each $R_1$ is a $C_1$ to $C_5$ substituted or unsubstituted hydrocarbyl having the same number of carbon atoms;
$^mM$ is a radioisotope; and
X is a linking domain comprising a functional group.

17. The complex of claim 16, further comprising a targeting vector conjugated to the linking domain.

18. The complex of claim 17, wherein the targeting vector is selected from the group consisting of peptides, antibodies, oligonucleotides, carbohydrates, lipids, and organic molecules.

19. The complex of claim 16, wherein each $R_1$ is methyl.

20. The complex of claim 16, wherein $^mM$ is a radioisotope of arsenic.

* * * * *